United States Patent
Shakur et al.

(10) Patent No.: US 10,602,942 B2
(45) Date of Patent: Mar. 31, 2020

(54) METHOD OF DETECTING ABNORMALITIES IN ECG SIGNALS

(71) Applicant: CAMBRIDGE HEARTWEAR LIMITED, Cambridge (GB)

(72) Inventors: Rameen Shakur, Cambridge (GB); Levin Chun Kiat Tan, Singapore (SG); Roberto Cipolla, Cambridge (GB)

(73) Assignee: CAMBRIDGE HEARTWEAR LIMITED, Cambridge (GB)

( * ) Notice: Subject to any disclaimer, the term of this patent is extended or adjusted under 35 U.S.C. 154(b) by 136 days.

(21) Appl. No.: 15/686,948

(22) Filed: Aug. 25, 2017

(65) Prior Publication Data
US 2019/0059763 A1 Feb. 28, 2019

(51) Int. Cl.
| A61B 5/04 | (2006.01) |
| A61B 5/0245 | (2006.01) |
| A61B 5/00 | (2006.01) |
| A61B 5/0452 | (2006.01) |
| A61B 5/024 | (2006.01) |

(Continued)

(52) U.S. Cl.
CPC ........ *A61B 5/04012* (2013.01); *A61B 5/0022* (2013.01); *A61B 5/0245* (2013.01); *A61B 5/02438* (2013.01); *A61B 5/0402* (2013.01); *A61B 5/046* (2013.01); *A61B 5/0452* (2013.01); *A61B 5/0456* (2013.01); *A61B 5/72* (2013.01); *A61B 5/725* (2013.01); *A61B 5/7267* (2013.01); *A61B 5/7485* (2013.01); *A61B 5/7264* (2013.01)

(58) Field of Classification Search
CPC ... A61B 5/04012; A61B 5/0456; A61B 5/046; A61B 5/0452; A61B 5/7264
See application file for complete search history.

(56) References Cited

U.S. PATENT DOCUMENTS

| 2003/0176795 A1 | 9/2003 | Harris et al. |
| 2009/0112110 A1* | 4/2009 | Zhang ............... A61B 5/04017 600/518 |

(Continued)

OTHER PUBLICATIONS

"Arrhythmia", NHS, London, UK, Jul. 8, 2015. [Online]. Available: http://www.nhs.uk/conditions/arrhythmia/Pages/arrhythmia.aspx.

(Continued)

*Primary Examiner* — Alyssa M Alter
(74) *Attorney, Agent, or Firm* — Tarolli, Sundheim, Covell & Tummino LLP

(57) ABSTRACT

We disclose herein a method of detecting abnormalities in electrocardiogram (ECG) signals, the method comprising receiving a set of ECG signals from an ECG device; amplifying only the peaks of at least some of the set of ECG signals to produce ECG beat markings from which a heart rate is derivable to detect an irregular rhythm between at least two ECG beats; extracting a single ECG beat from the set of ECG signals from the ECG device by using said ECG beat markings; feeding the extracted single ECG beat into a first neural network; producing, at the first neural network, a compact representation of the extracted single ECG signal so as to generate a feature extraction output; and using, at a second neural network, the feature extraction output from the first neural network to generate a score associated with the abnormalities in the ECG signals.

19 Claims, 15 Drawing Sheets

(51) Int. Cl.
A61B 5/0402 (2006.01)
A61B 5/0456 (2006.01)
A61B 5/046 (2006.01)

(56) References Cited

U.S. PATENT DOCUMENTS

2012/0179055 A1 7/2012 Tamil et al.
2015/0164349 A1 6/2015 Gopalakrishnan et al.

OTHER PUBLICATIONS

"The AF report. Atrial fibrillation—preventing a stroke crisis," Atrial Fibrilla¬tion Assoc., Warwickshire, Anticoagulation Europe, Kent, UK, Apr. 12, 2012. [Online]. Available: http://www.preventaf-strokecrisis.org/files/files/The AF Report 14 April 2012.pdf.
K. Carroll, S. Murad, J. Eliahoo, and A. Majeed, "Stroke incidence and risk factors in a population-based prospective cohort study," Office for Na¬tional Statistics, Newport, South Wales, UK, Rep. Health Statistics Quarterly 12, 2001. [Online]. Available: http://www.ons.gov.uk/ons/rel/hsq/health-statistics-quarterly/no-12-winter-2001/stroke-incidence-and-risk-factors-in-a-population-based-prospective-cohort-study.pdf.
C. Marini et al., "Contribution of atrial fibrillation to incidence and outcome of ischemic stroke: results from a population-based study," Stroke, vol. 36, pp. 1115-1119, 2005. DOI: 10.1161/01.STR.0000166053.83476.4a.
D. M. Lloyd-Jones et al., "Lifetime risk for development of atrial fibrillation: the Framingham heart study," Circulation, vol. 110, No. 9, pp. 1042-1046, Aug. 31, 2004. DOI: 10.1161/01.CIR.0000140263.20897.42.
G. Y. H. Lip and H. S. Lim, "Atrial fibrillation and stroke prevention," The Lancet Neurology, vol. 6, No. 11, pp. 981-993, Nov. 2007. DOI: 10.1016/S1474-4422(07)70264-8.
M. Cesarelli, P. Bifulco, and M. Bracale, "An algorithm for the detection of the atrial fibrillation from the surface ECG for an of home-care evaluation of the implanted atrial defibrillators," in Proc. Mediterranean Conf. Medical and Biological Eng. and Computing, Cyprus, 1998. ARK: /87278/s6np23vh.
M. Carrara et al., "Classification of cardiac rhythm using heart rate dynamical measures: validation in MIT-BIH databases," J. of Electrocardiology, vol. 48, No. 6, pp. 943-946, Nov.-Dec. 2015. DOI: 10.1016/j.electrocard.2015.08.002.
J. S. Healy et al., "Subclinical atrial fibrillation and the risk of stroke," The New England J. of Medicine, vol. 366, No. 2, pp. 120-129, Jan. 12, 2012. DOI: 10.1056/NEJMoa1105575.
PhysioNet, The MIT-BIH Atrial Fibrillation Database. [Online]. Available: https://physionet.org/physiobank/database/afdb/.
G. B. Moody and R. G. Mark, "A new method for detecting atrial fibrillation using R-R intervals," Comput. in Cardiology, vol. 10, pp. 227-230, 1983.
PhysioNet, The MIT-BIH Sinus Rhythm Database. [Online]. Available: https:// physionet.org/physiobank/database/hsrdb/.
M. Carrara, et al., "Heart rate dynamics distinguish among atrial fibrillation, normal sinus rhythm and sinus rhythm with frequent ectopy," Physiological Measurement, vol. 36, No. 9, pp. 1873-1888, Sep. 2015. DOI: 10.1088/0967¬3334/36/9/1873.
S. Ladavich and B. Ghoraani, "Developing an atrial activity-based algorithm for detection of atrial fibrillation," in 36th Annu. Int. Conf. IEEE Eng. in Medicine and Biology Soc., Chicago, IL, USA, 2014, pp. 54-57. DOI: 10.1109/EMBC.2014.6943527.
I. Giller and E. D. Ubeyli, "ECG beat classifier designed by combined neural network model," Pattern Recognition, vol. 38, No. 2, pp. 199-208, Feb. 2005. DOI: 10.1016/j.patcog.2004.06.009.
T. Chou, Y. Tamura, and I. Wong, "Detection of atrial fibrillation in ECGs," Final Project, Dept. Comput. Sci., Stanford Univ., Stanford, CA, USA, 2008. [Online]. Available:http://cs229.stanford.edu/proj2008/ChouTamuraWong-DetectionOfAtrialFibrillationInECGs.pdf.
S. Karpagachelvi, M. Arthanari, and M. Sivakumar, "ECG feature extraction techniques—a survey approach," Int. J. of Comput. Sci. and Inform. Security, vol. 8, No. 1, Apr. 2010. arXiv: 1005.0957.
A. L. Maas, A. Y. Hannun, A. Y. Ng, "Rectifier nonlinearities improve neural network acoustic models," Proc. 30th Int. Conf. Mach. Learning, vol. 28 Atlanta, GA, USA, 2013. [Online]. Available: http://ai.stanford.edu/~amaas/papers/relunhybridnicml2013nfinal.pdf.
L. J. P. van der Maaten and G. E. Hinton, "Visualising high-dimensional data using t-SNE," Journal of Mach. Learning Res., vol. 9, pp. 2579-2605, Nov. 2008.
Jambukia, Shweta H., Vipul K. Dabhi, and Harshadkumar B. Prajapati. "Classification of ECG signals using machine learning techniques: A survey." Computer Engineering and Applications (ICACEA), 2015 International Conference on Advances in. IEEE, 2015.
Patel, Abhilasha M., Pankaj K. Gakare, and A. N. Cheeran. "Real time ECG feature extraction and arrhythmia detection on a mobile platform." Int. J. Comput. Appl 44.23 (2012): 40-45.
PCT International Search Report and Written Opinion for corresponding International Application Serial No. PCT/EP2018/071812, pp. 1-19.

* cited by examiner

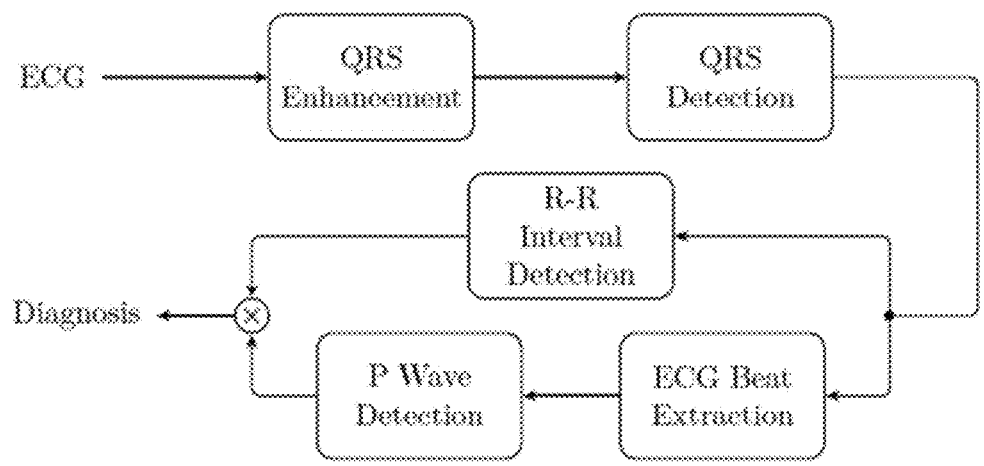
Fig. 6
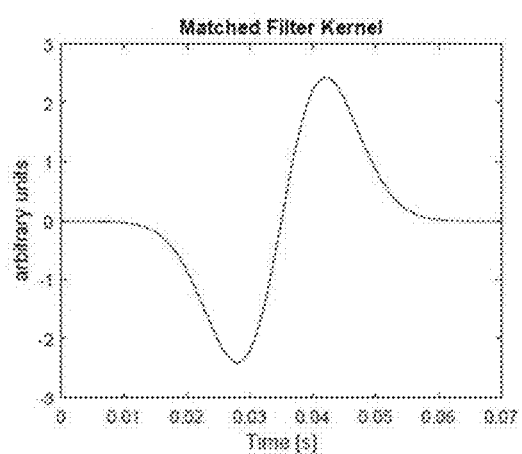 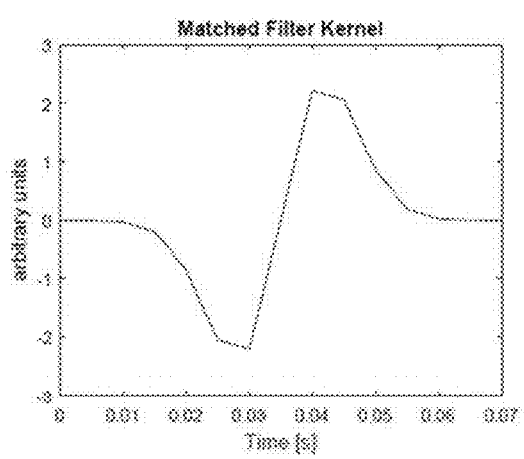
Fig. 7         Fig. 8

METHOD OF DETECTING ABNORMALITIES IN ECG SIGNALS

FIELD OF THE INVENTION

The present invention relates to a method and system for detecting abnormalities in electrocardiogram (ECG) signals.

BACKGROUND TO THE INVENTION

Every year, more than 2 million people in the UK are affected by cardiac arrhythmia (heart rhythm abnormalities) which can lead to stroke, cardiac arrest, or even sudden cardiac death. In particular, atrial fibrillation (AF) is responsible for 20% of all strokes caused by clots (ischemic stroke). The population of AF patients is around 1.5 million in the UK alone.

However, early detection allows the commencement of treatment which can allow patients to lead a normal life, and thus is of great importance. Yet, AF in early stages occurs sporadically and inconsistently in short episodes, termed "paroxysmal AF", which may be difficult to detect in short tests. This is before developing into more sustained episodes, termed "persistent AF". In these early stages, round-the-clock monitoring is necessary to capture these short episodes.

Existing solutions are adequate in detecting what is known as "clinical AF", by operating on the order of minutes and diagnosing based on the fraction of time spent in AF and non-AF. This is to reduce false alarms. However, very short episodes of AF that may be "subclinical" during the paroxysmal stage may go undetected in such algorithms.

Turning to more details of AF, this is the most common type of cardiac arrhythmia, and is a condition of the heart whereby the atria—upper chambers of the heart—do not coordinate well to pump blood through the body. This may allow blood clots to form, which can lead to a stroke when they travel to the brain.

Having AF increases the risk of stroke in patients by 5 times [1], and the overall risk of death in patients by twice [2]. A stroke afflicts 100,000 people per year in England and Wales [3] (equivalent to one person every 5 minutes), and 20% of all strokes caused by such clots (known as an ischemic stroke) result from AF [4]. An estimated 1.5 million people in the UK have AF currently [2], and the NHS spends over £2.2 billion a year on treating AF and AF related illnesses [2]. By the time adults reach 40 years of age, they have a lifetime risk of about 25% of developing AF [5].

If AF is detected, patients may be put on treatment and medication like blood thinners (Warfarin in particular), which can reduce the risk of stroke by up to two thirds [6], and the risk of death by one third without significantly increasing the risk of major bleeding [2]. Stroke patients require a long recovery, and many suffer permanent neural damage. This has a significant impact on the workforce and economy, estimated to be around £2.4 billion per annum [2].

FIG. 1 illustrates a basic electrocardiograph (ECG) signal. This has several points which are labelled as P, Q, R, S, and T. These features arise from the electrical signals that pass through the different heart muscles in a procedural manner to allow the heart to pump blood normally. The voltage and time statistics—height, width, and time intervals of the various features—are key to diagnosing abnormalities in the heart rhythm. Most significantly, the P wave is the result from activity in the atria.

FIG. 2 illustrates a series of ECG signals which may be used for the detection of AF by doctors in clinics. They are, in order of reliability:

Irregularly irregular R-R intervals
Missing P waves
Presence of fibrillatory waves in the ECG base line.

Using each indicator on its own has its setbacks, but work well when used altogether.

Irregular R-R intervals, while being the easiest to detect in most circumstances, may not indicate AF in some cases, as there are various other arrhythmia that also exhibit this.

Missing P waves are difficult to observe in cases where there are high noise levels which can obscure the baseline of the ECG signal, or if the ECG leads are not placed in positions to efficiently pick up electrical signals from the atria. There are also other arrhythmia that exhibit delayed, or advanced P waves, complicating the detection.

Fibrillatory waves on the ECG base line are the hardest to observe because they are irregular, and vary in amplitude from coarse to fine [7]. Thus they are easily obscured by noise and other interference such as electrical activity from muscles. Owing to this, fibrillatory waves are considered a "soft marker" for AF.

To make matters worse, AF occurs sporadically—termed "paroxysmal AF"—in patients in the early stage, before becoming continuous—termed "persistent AF"—in their later age. While in its early stage, a patient may only exhibit AF under specific physiological conditions, e.g. when patients are under physical stress, if they consume alcohol, etc, and these sporadic episodes of AF may occur for very short periods of time on the order of seconds. This means that for early detection, round-the-clock monitoring is needed so that there is the opportunity to capture these short episodes of AF.

Computer algorithms already exist for the detection of AF. The usual approach is to diagnose AF by a threshold of AF burden (i.e. percentage of beats which are AF in a certain time window), as seen in [8], to reduce false positives and diagnosis. This works well for the diagnosis of what is termed as "clinical AF".

However, during the stage of paroxysmal AF, such episodes can be short enough that they can be passed over by such detection algorithms. These very short episodes are termed "subclinical AF". According to a recent investigation [9], being diagnosed with subclinical AF places an individual at 5.5 times the risk of developing clinical AF, and 2.5 times the risk of stroke, both within a period of approximately 2.5 years. Early detection of AF can thus have significant impact, but requires acute accuracy in the algorithm, and at high resolutions.

SUMMARY OF THE INVENTION

Embodiments of the invention aim to devise a system solution consisting of a lightweight and cost-effective wearable that is able to perform at least 24 hours of ECG monitoring between charges, and uploads its data to a server in real time. An algorithm is then run on the data to detect abnormalities which are then highlighted and presented to the cardiologist, reducing the need to sift through enormous amounts of data by hand, allowing extensive deployment in the general population. The focus is on early detection of AF, and as such, even extremely short episodes of AF (e.g. between 2 beats) ideally should be identified.

Generally speaking, a typical request for ECG monitoring starts with a consultation, followed by attachment of the device to the patient. After 24 or 48 hours, another consultation is done to download the data, followed by analysis in software and by hand. If there is a need to gather more data, the process is repeated. By having a real-time stream to the server, the second consultation need not take place until enough data has been gathered. Severe life-threatening situations can also be monitored and acted upon immediately, such as dispatching an ambulance to a patient in cardiac arrest.

In other words, the aim of the embodiments of the invention is generally to develop an end-to-end solution comprising a cheap and lightweight wearable device that uploads its data to a server in real time. A beat-level resolution technique/algorithm is then run on the data which highlights abnormalities (AF) and presents it to the cardiologist.

Broadly speaking, AF is diagnosed by the two most prominent symptoms in the ECG trace, which is characterised by an irregular heart rhythm, and a missing feature on the signal known as the P wave. The algorithm developed in the embodiments of the present invention for analysis performs in several stages to achieve diagnosis at beat-level resolution, and is trained on a variety of data from for example the PhysioNet PhysioBank Archives. The MIT-BIH AF and NSR databases are generally used. However, embodiments of the invention is not restricted to the use of such databases. Neural networks can be trained in other ways.

According one aspect of the present invention, there is provided a method of detecting abnormalities in electrocardiogram (ECG) signals, the method comprising:
 receiving a set of ECG signals from an ECG device;
 amplifying only the peaks of at least some of the set of ECG signals to produce ECG beat markings from which a heart rate is derivable to detect an irregular rhythm between at least two ECG beats;
 extracting a single ECG beat from the set of ECG signals from the ECG device by using said ECG beat markings;
 feeding the extracted single ECG beat into a first neural network;
 producing, at the first neural network, a compact representation of the extracted single ECG signal so as to generate a feature extraction output; and
 using, at a second neural network, the feature extraction output from the first neural network to generate a score associated with the abnormalities in the ECG signals.

The irregular rhythm may be detected from an irregular R-R interval flag, and the score generated at the second neural network may determine the presence or absence of a P-wave in the ECG signals.

The method may further comprise combining the irregular R-R interval flag with the score from the second neural network for identifying abnormalities in the ECG signals.

Embodiments of the invention enable the detection of abnormalities associated with the irregular R-R interval and the detection of the presence or absence of P-waves in ECG signals in a more efficient and improved way. The machine learning technique proposed by the embodiments of the invention is capable of providing a beat level resolution for detecting abnormalities which is otherwise not possible in conventional techniques. The machine learning technique provides more sensitive results in terms of AF detection which are generally not detectable in a manual detection approach.

The amplifying only the peaks of at least some of the set of ECG signals is performed by a matched filtering technique. The irregular R-R interval is detected during the matched filtering step. The matched filtering technique is used to increase signal to noise ratio (SNR). An appropriate kernel for matched filtering is generally parametrised for generation of any length required for tuning purposes and to be compatible with data of different sampling frequencies. Generally speaking, a kernel width of about 0.07 s is advantageous for picking up the QRS complexes.

The matched filtering technique may reduce a base line wander of the set of ECG signals. The matched filtering technique may use an algorithm comprising a first derivative of a Gaussian and/or a second derivative of a Gaussian. Using the first derivative of a Gaussian is advantageous because it meets the requirements and looks like a typical QRS complex in an ECG signal.

The method may further comprise applying an additive thresholding technique on the matched filtered signal which generates the ECG beat markings. A suitable value for the thresholding can generally be used. The result is a series of QRS beat markings from which time statistics can be extracted. In one embodiment, for a rhythm to be classified as irregular, a window of, for example, 5 beats (4 intervals) is created and swept across the whole record. The difference in R-R intervals are then added together. If the difference exceeds a certain threshold, the whole window of beats is classified as irregular. Advantageously, the irregular R-R interval detection algorithm only does addition and subtraction to compute the absolute sum of all differences for every 4 intervals. This is dependent on heart rate, which is independent of sample rate, and hence of computational complexity O(1).

The extracting the single ECG beat may be conducted by cutting between two consecutive R-R intervals.

The method may further comprise scaling the extracted single beat through resampling so that it fits into a predetermined number of samples. In one embodiment, the waveform of the single beat also has its mean amplitude subtracted, its minimum taken away to ensure the whole waveform is positive, and finally uniformly scaled in amplitude to only be from 0 to 1.

At least one of the first and second neural networks may be a feed forward artificial neural network.

The first neural network may be trained as an auto-encoding neural network having a pinch point. It will be appreciated by the skilled person that the pinch point can also be termed as a bottleneck. The compact representation of the single ECG beat may be obtained by splitting the auto-encoding neural network at the pinch point. The compact representation of the single ECG beat may be obtained by using a front end of the auto-encoding neural network. In one embodiment, the auto-encoder structure is 201-100-20-100-201, but other structures are possible. The auto-encoder network uses a leaky Rectified Linear Unit activation function. This function is fast to compute, and does not suffer from the vanishing/exploding gradient problem as compared to the classic sigmoid function.

The output from the pitch point of the auto-encoding network may be a feature vector of a predetermined size, and optionally the feature vector may generate a plurality of clusters. Features associated with abnormalities may be grouped in at least some clusters. The feature extraction very cleanly separates the AF beats from the normal (non AF) beats.

The second neural network may be a trained classifier network which generates the score associated with the abnormalities relating to the presence or absence of P-wave in ECG signals.

The method may further comprise training a support vector machine with a Gaussian algorithm to compare the results from the classifier network.

The second neural network may be a classifier network which determines any one of:
(1) atrial fibrillation (AF);
(2) inverted T-waves;
(3) deep Q-waves; and/or
(4) deep S-waves.

The method may further comprise a plurality of second neural networks, each determining a separate symptom from the following list:
(1) atrial fibrillation (AF);
(2) inverted T-waves;
(3) deep Q-waves; and/or
(4) deep S-waves.

According to a further aspect of the present invention, there is provided a system for detecting abnormalities in electrocardiogram (ECG) signals, the system comprising:
an ECG device configured to obtain a set of ECG signals;
a mobile device configured to receive ECG signals from the ECG device;
a server configured to receive ECG data from the mobile device; and
a processing unit configured to process the set of ECG signals from the ECG device and detect abnormalities in the ECG signals.

The processing unit may be located within the ECG device or the server.

The processing unit may comprise:
an irregular rhythm detector for amplifying only the peaks of at least some of the set of ECG signals to produce ECG beat markings from which a heart rate is derivable to detect an irregular rhythm between at least two ECG beats;
a beat extractor for extracting a single ECG beat from the set of ECG signals from the ECG device by using said ECG beat markings;
a first neural network for receiving the extracted single ECG beat and for producing a compact representation of the extracted single ECG signal so as to generate a feature extraction output; and
a second neural network for using the feature extraction output from the first neural network to generate a score associated with the abnormalities in the ECG signals.

BRIEF DESCRIPTION OF THE DRAWINGS

Some preferred embodiments of the invention will now be described by way of an example only and with reference to the accompanying drawings, in which:

FIG. 6 illustrates a flow diagram showing an algorithm structure for AF detection and classification;

FIG. 7 illustrates a derivative of a Gaussian kernel according to one embodiment;

FIG. 8 illustrates a kernel spanning 0.07 s at 200 Hz sampling frequency according to one embodiment;

DETAILED DESCRIPTION OF THE PREFERRED EMBODIMENTS

I. An Example of an Overall System Architecture

Figure 1:
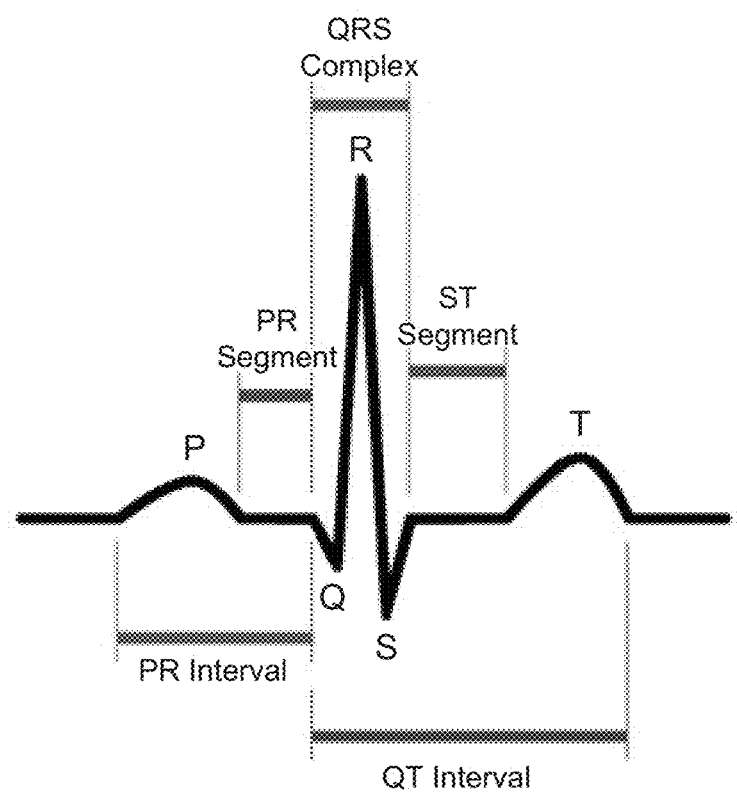
FIG. 1 illustrates a basic electrocardiograph (ECG) signal.
Figure 2:
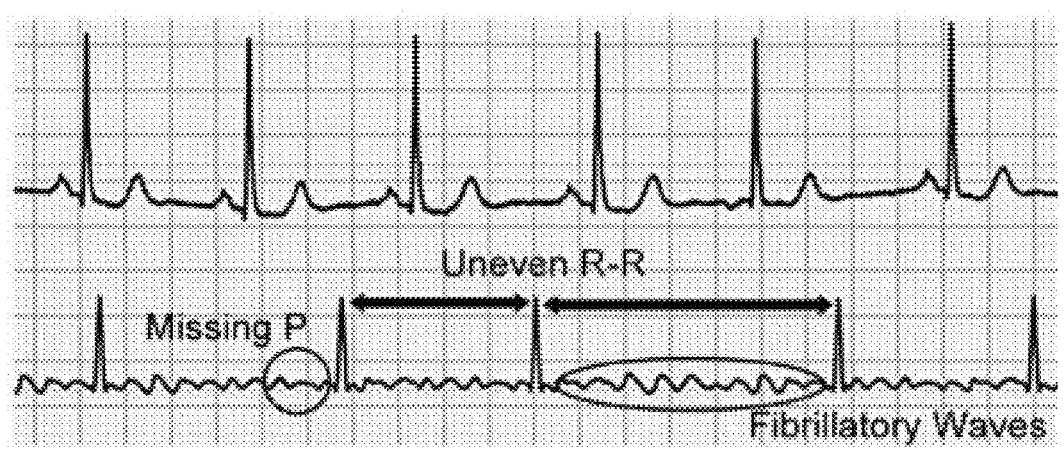
FIG. 2 illustrates a series of ECG signals which may be used for the detection of AF by doctors in clinics.
Figure 3:
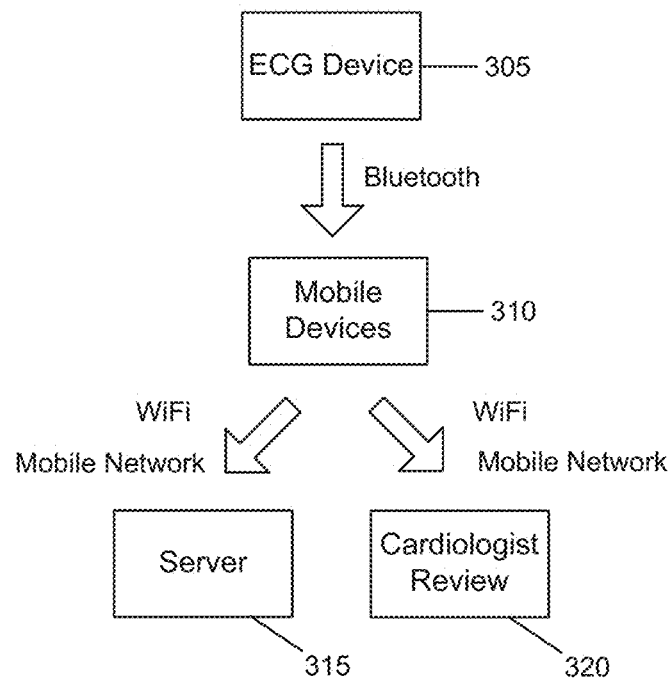
FIG. 3 illustrates an exemplary overall system architecture according to one embodiment of the present invention.

FIG. 3 illustrates an exemplary overall system architecture according to one embodiment of the present invention. In one example, a wearable ECG device 305 communicates, for example, by Bluetooth to a mobile device 310 (e.g. a mobile phone) carrying an application that buffers and uploads the data to a server 315 through mobile or Wi-Fi networks. This will ensure the wearable device is as light-weight as possible. The phone 310 may also perform some rudimentary analysis of the incoming signals to check for emergencies like cardiac arrest and directly send an alert to the cardiologist 320. Otherwise, the server 315 performs most of the analysis on the incoming data, and then highlights regions of interest for the cardiologist to inspect later, greatly reducing the workload on the cardiologist 320.

In one embodiment, the ECG device 305 includes a processing unit which is used to detect abnormalities with the ECG signal. For instance, the processing unit may have a matched filter, an extractor, and neural networks to detect the abnormalities (or cardiac arrhythmia) in the ECG signals. Alternatively, the processing unit could be located within the server 315 as well.

II. An Example of a Network Architecture

Broadly speaking, the network architecture is developed as a test bed. In order to aid in rapid development of the system, a commercial off-the-shelf product was chosen. For example, the BITalino [11] is a small device comprising several modules that can be assembled together depending on the required usage. For this system, for example, the microcontroller, Bluetooth, and ECG modules were used. This device is small enough to be tucked into a small sewn pocket underneath a t-shirt. It will be appreciated that other types of devices having different arrangements could also be used within the scope of the present invention.

Figure 4:
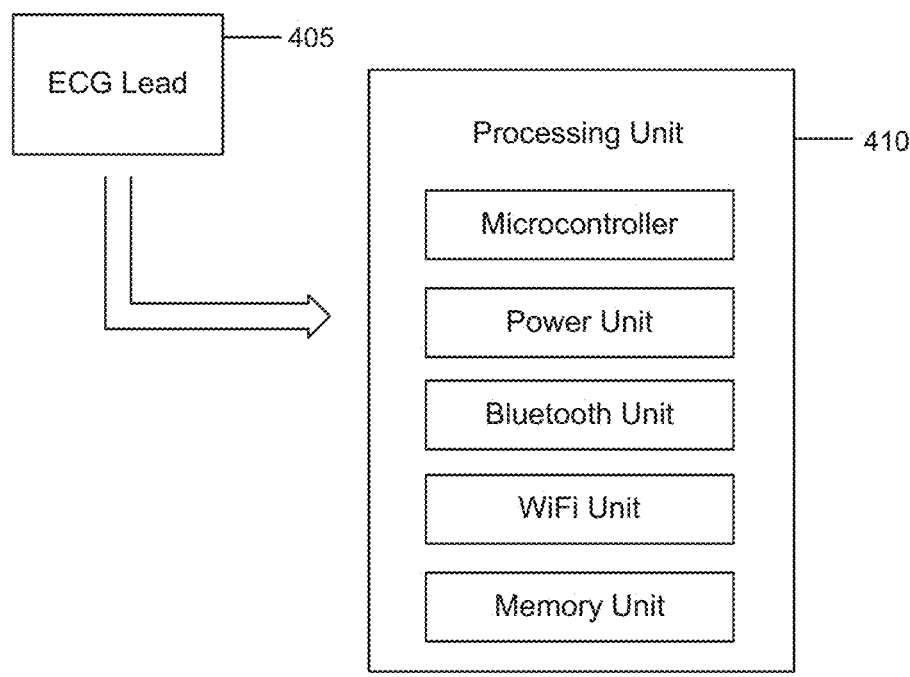
FIG. 4 illustrates a schematic representation of a network architecture according to one embodiment of the present invention.

FIG. 4 illustrates a schematic representation of a network architecture. This arrangement includes a ECG lead or module 405 coupled with a processing unit 410. The processing unit 410 includes a microcontroller, a Bluetooth unit, a WiFi unit, and preferably a memory unit. In this embodiment, the processing unit 410 is located within an ECG module 405.

Generally speaking, the ECG module 405 is a simple operational amplifier which operates in differential mode to amplify ECG signals from the user's skin. This feeds, for example, to the 10-bit ADC on the microcontroller sampling at, for example, 1 kHz, which then transmits via the Bluetooth module to an Android cell phone. It will be appreciated that cell phone running on other operating system (e.g. iOS) could also be used. The lithium polymer battery on the wearable has been tested to power the device for approximately 20 hours on a single charge which falls slightly short of the 24 hours targeted. If a battery is doubled, the device still remains very small, while most likely be able to monitor up to 40 hours on a single charge, which is sufficient. Embodiments of the invention is not restricted to the use of lithium polymer battery—other suitable types of batteries could be used.

In one example, with only one ECG module, only one ECG channel can be monitored. This can be easily expanded to several channels as needed. It would be apparent to the skilled person that more than one ECG module can also be used as necessary. The invention is not restricted to the use of one ECG module only.

A suitable smart phone application, for example the Bitadroid [12], can be used in the BITalino device. Since it is desirable to live stream to the server, the application was modified in Android Studio, and generally sends an ASCII file of readings every 10 seconds to the specified server. However, the invention is not restricted to sending readings every 10 seconds to the specified server.

A simple server which receives the upload from the phone application was developed for example in Python 3, using Flask, with a MySQL database. It receives the file uploaded and appends it to a table which is created each new transmission session. Python 3 was chosen for its ease and speed of development. However, the invention is not restricted to the use of Python 3—other application platforms could be used as necessary.

The Flask server also serves up a webpage for live viewing of the incoming data stream (not shown here). This is generally implemented in HTML, using JavaScript libraries jQuery for asynchronous fetching of data from the server, and D3.js for presentation of the graph. A graph has generally been made to plot on "ECG paper" which cardiologists are very familiar with, to aid in interpretation. In one example, the overall lag between the ECG trace observed on the phone and on the computer, is approximately 30 seconds or longer in practice due to the various buffers in the pipeline. Other timing lag could also be possible.

Analysis is then done, in one example, via MATLAB. Other techniques of doing a similar analysis are within the scope of the invention.

III. Methodology Steps

Figure 5:
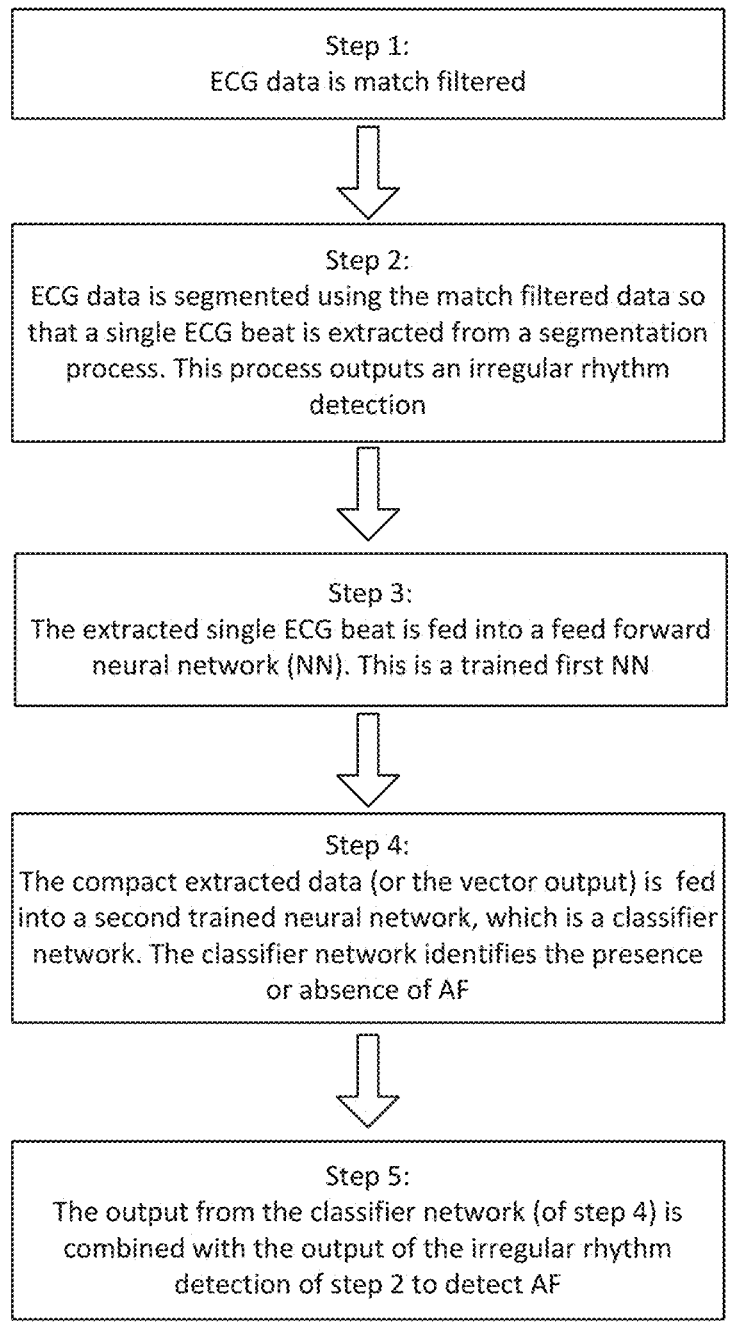
FIG. 5 illustrates the overall methodology steps for detecting abnormalities in ECG signals according to one embodiment of the present invention.

FIG. 5 illustrates the overall methodological steps for detecting abnormalities in ECG signals according to one embodiment of the present invention. The steps are described in detail as follows:

In step 1: a matched filtering technique is applied on the incoming ECG signals. For example, the incoming signal is convolved with a kernel (or algorithm) designed to amplify only the peaks of the ECG which is termed as the matched filtering. This then allows ECG beats to be marked (or produces ECG beat markings) from which the heart rate can be derived to check for irregular rhythm, for example, to detect irregular R-R intervals between two consecutive ECG beats.

In step 2: the beat markings are also used to segment the ECG trace and extract traces of individual heartbeats, which are then fed into a neural network for diagnosis of the P wave.

In step 3: the neural network (or the first neural network) is trained initially as an auto-encoder with a pinch point of width of, for example, 20 nodes so that a compact representation of the signal is achieved. Here the auto-encoder network receives the original ECG signals but follows the trend derived from the matched filtered technique in step 1. By splitting the trained network at the pinch point, the encoding part of the network acts as a feature extractor to generate a vector of, for example, 20 features. It will be appreciated that the number of nodes in this step is not restricted to 20—other numbers of suitable nodes can be chosen. This feature extraction has been observed to group beats of similar characteristics together and thus provides a clear distinction in feature space that has the potential for diagnosis of other arrhythmias and not just AF.

In step 4: for classification, another smaller neural network (or the second neural network) is trained using the feature vector output from the first neural network. This was compared to a support vector machine and was found that both performed almost equally, with the neural network being very substantially better. Advantageously, at the optimum, the true positive rate is about 88.8% with a false positive rate of about 6.5%.

In step 5: output from the neural network classifier is combined together with the output from the irregular rhythm detector for AF diagnosis. This has been tested and shown to be comparable to the competing legacy product of the Holter Monitor software at worst and significantly better at best, with sensitivity (true positive) of 91% to 99% compared to 95%, and specificity (1-false positive) of 76% to 99% compared to 75%. Advantageously, this provides improvement over the conventional techniques.

In summary, analysis of the diagnosis of the algorithms developed has shown that it is able to diagnose very short episodes of AF or non-AF in the middle of longer episodes of non-AF or AF respectively, which were not marked in the database as such, likely due to what is thought to be insignificant (subclinical), or missed. This fulfils the objective of achieving beat-level resolution in the embodiment of the present invention.

Overall, the end-to-end solution has been demonstrated in the present invention, with potential to extend into classification of other cardiac arrhythmia, and paving the way for more studies on diagnosis and significance of subclinical AF. The computational complexity of the algorithm (tens of thousands of multiplications and additions per second) is low enough that it should present no trouble for modern day processors.

IV. Methodology for AF Detection and Classification

Although the primary focus of the embodiments of the present invention is to detect AF, the most common form of cardiac arrhythmia, it is also possible to detect other type of arrhythmia from the technique/methodology/system proposed by the present invention. Arrhythmia is generally diagnosed by looking at time statistics between heartbeats, within each heartbeat, and the various features (P, Q, R, S, T) of each beat.

The detection of arrhythmia is broadly divided into two parts—detection of abnormal time intervals between beats, and detection of anomalies within the beat. It has been divided as such due to the different challenges that each method faces. All signal processing is generally done in MATLAB. However, other similar software could be used the same purpose.

FIG. 6 illustrates a flow diagram showing an algorithm structure for AF detection and classification. In this diagram, the QRS enhancement and QRS detection relate to amplifying the peaks of the ECG signals which are used to detect R-R intervals.

In one embodiment, the data trained on are 1 hour extracts from each record from the PhysioNet PhysioBank Archives, which contain large amounts of data of normal and abnormal ECGs in several databases. The databases used are the MIT-BIH Atrial Fibrillation (AF) Database [13] (described in [14]), and the MIT-BIH Normal Sinus Rhythm (NSR) Database [15]. The waveforms in these databases have their rhythm annotated by machine algorithm, and broad annotations marking sections of abnormalities vs NSR by hand, but not down to beat level. For the purposes of creating the full system, these annotations are used as a guide, but not taken as absolute, since the resolution of the annotations are not sufficient. Only records with lead I, II, or III waveforms are used for consistency. (See Section VI. D. for a complete discussion about the database and Section VI. E. for discussion regarding prevention of overtraining). It will be appreciated that the invention applies to other databases as well as other sources. Embodiment of the invention are not restricted to these databases.

IV. A. Detection of Inter-Beat Anomalies

Generally speaking, the most obvious sign of cardiac arrhythmia is from the R-R intervals. QRS complexes are the most easily identifiable part of the ECG trace, being huge spikes that show through even large amounts of noise.

However, ECG traces generally have a wandering baseline, and thus a simple thresholding of the signal is insufficient to detect the QRS complexes. Since all that is required is the QRS complex position in time, matched filtering is used to increase the signal to noise ratio (SNR).

The appropriate kernel for matched filtering is generally parametrised for generation of any length required for tuning purposes and to be compatible with data of different sampling frequencies. It also has to be balanced so that baseline wander is rejected.

FIG. 7 illustrates a derivative of a Gaussian kernel. The first derivative of a Gaussian was found to work generally well, since it met the requirements and looks like a typical QRS complex in an ECG signal. Another possible kernel is the second derivative of a Gaussian.

FIG. 8 illustrates a kernel spanning 0.07 s at 200 Hz sampling frequency. It was demonstrated that a kernel width of about 0.07 s was found to be generally better for picking up the QRS complexes. Note that the amplitude of the kernels does not matter since the SNR in the resulting convolution is unaffected.

Figure 9:
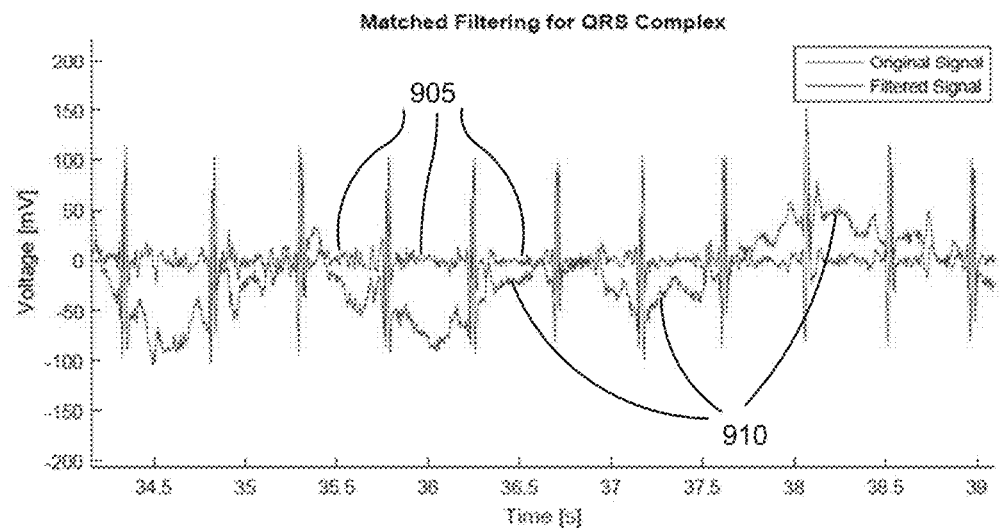
FIG. 9 illustrates a comparison between the matched filtered signal and the original ECG signal according to one embodiment.

FIG. 9 illustrates a comparison between the matched filtered signal 905 and the original ECG signal 910. As can be seen, the resulting filtered signal 905 has very pronounced spikes located at the R peak of the QRS complex and has no baseline wander. Adaptive thresholding is then run on the filtered signal 905 as such.

Figure 10:
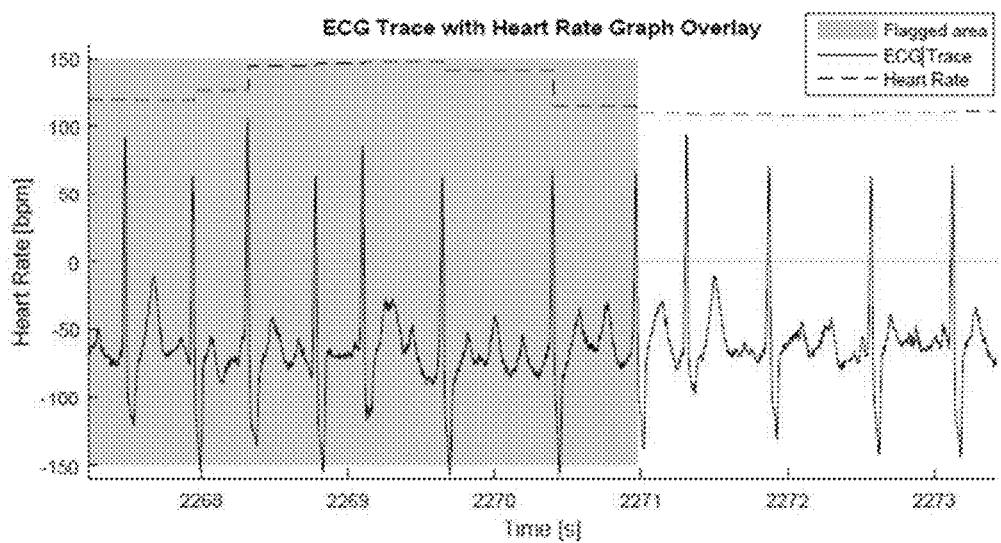
FIG. 10 shows an example of a rhythm being flagged purely based on irregular R-R intervals.

FIG. 10 shows an example of a rhythm being flagged purely based on irregular R-R intervals. Section of irregular heart rhythm is flagged by the processing algorithm (shaded area). Note that the amplitude scale for the ECG signal is arbitrary. The result is a series of QRS beat markings from which time statistics can be extracted. In one example, for a rhythm to be classified as irregular, a window of 5 beats (4 intervals) is created and swept across the whole record. The difference in R-R intervals are then added together. If the difference exceeds a certain threshold, the whole window of beats is classified as irregular.

In one embodiment, the values used were found empirically by Receiver Operating Characteristic (ROC) curves, and adjusting parameters to compromise between not flagging the waveforms from, for example, the NSR database [15], while still flagging those in the AF database [13]. At the same time, the wave forms are inspected to ensure that there were very few false flags due to errors in QRS detection. It will be appreciated that the invention is not restricted to the use of NSR database or AF database. Any other suitable source or database could be used for the same purposes.

Figure 11:
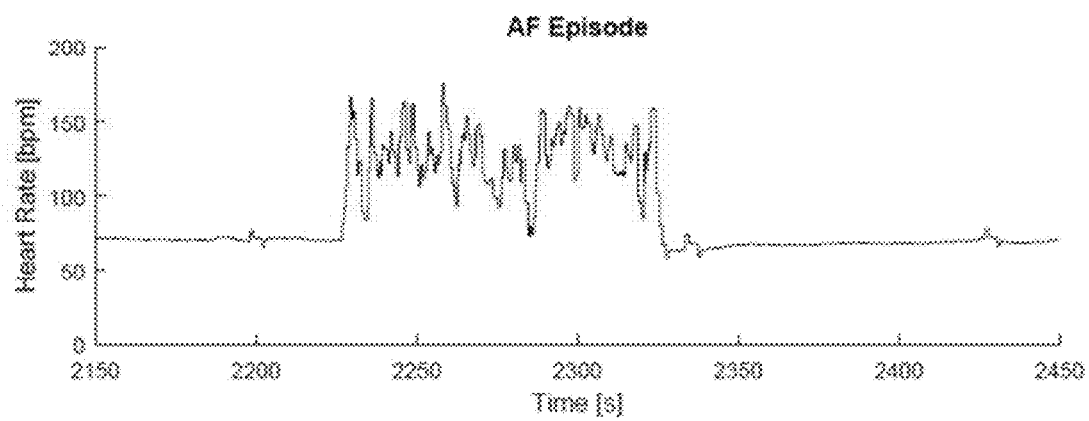
FIG. 11 illustrates an example of AF episode ("noisy" segment) seen in the heart rate plot.

FIG. 11 illustrates an example of AF episode ("noisy" segment) seen in the heart rate plot. Uneven R-R intervals can be readily recognised in AF records due to the sudden "noise" seen in a heart rate plot.

The above method is advantageous because it is very simple, with more reliance on the intra-beat anomaly detection.

IV. B. Feature Extraction of Single ECG Beats

While identification of irregular rhythm is relatively simple due to the very strong R peak, the visual inspection of the individual beat waveforms to reveal details about what is unusual about it is not immediately apparent how it translates into statistics of the signal. This is made worse by noise, electrical activity from muscles, a wandering baseline, and changing skin conductivity over time and from person to person. These can obscure the other more subtle features of an ECG beat.

In classification tasks like this, the usual approach is to employ a form of feature extraction which reduces the dimensionality of the data while retaining important characteristics to enable a classifier to function well. While speech and vision have much literature and a very long history of feature extraction research, ECG signals have comparatively few. Signal statistics [17], Fourier transforms [7], and wavelet transforms [18] have all been attempted with varying degrees of success, but the better results have been known to come from a combination of all those features combined [19]. This seems to suggest that ECG waveforms have richer features than any particular common method of feature extraction can hope to extract.

The present invention generally proposes to use Feed Forward Artificial Neural Networks (from here on referred to just as neural networks) for feature extraction.

The usual way of using a neural network is to choose what data to pass to it. A sliding window is generally inappropriate because the ECG features would be non-static, being fed to different points of the network, thus not allowing parts of the network to specialise. This can cause difficulty in convergence. A static window centred on a single beat, however, generally works well, and this is what is generally used. However, the invention is not restricted to this technique only—other approaches are equally applicable.

From the QRS markings generated by the algorithm in the previous section (IV. A.), a single ECG beat (FIG. 13) is extracted by cutting between two consecutive R-R intervals. This waveform is then scaled through resampling so that it fits into 200 samples, chosen because at low heart rates of 40 bpm, this corresponds to a sample rate of −133 Hz, which is still well above the upper band limit of 40 Hz (Nyquist of 80 Hz) on ECG equipment used in the PhysioNet database [13]. The scaling factor is appended as the 201st sample so that the neural network is "aware" of the actual duration of the waveform.

The waveform also has its mean amplitude subtracted, its minimum taken away to ensure the whole waveform is positive, and finally uniformly scaled in amplitude to only be from 0 to 1.

Figure 12:
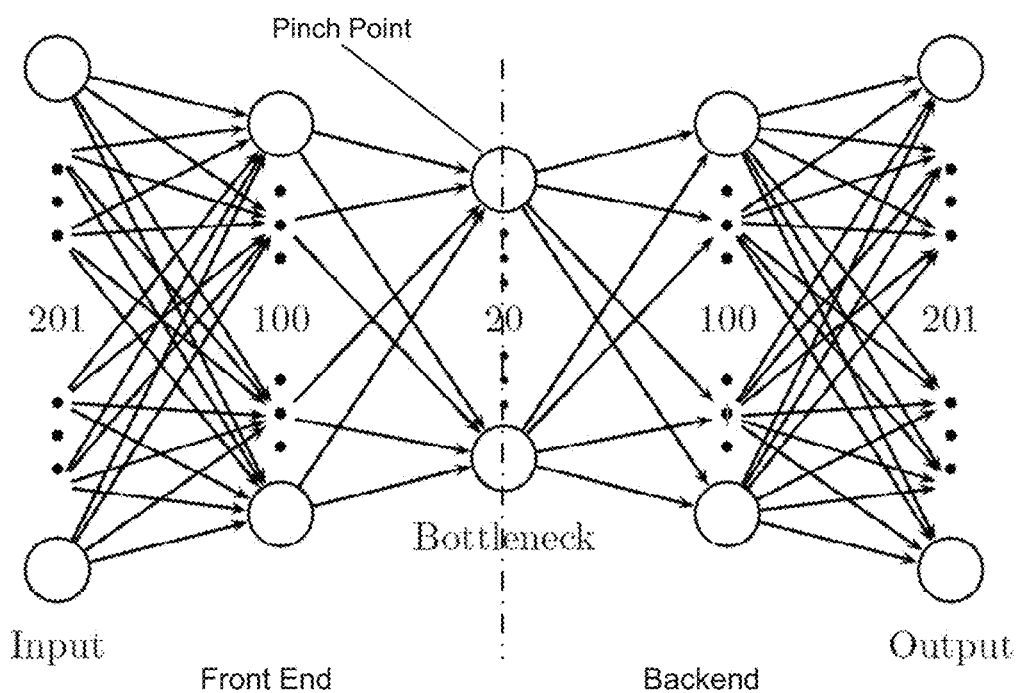
FIG. 12 illustrates an auto-encoder neural network structure (without showing all the connections) according to one embodiment.

FIG. 12 illustrates an auto-encoder neural network structure (without showing all the connections). The auto-encoder structure of 201-100-20-100-201 (FIG. 12) is formed with the (fully connected) neural network using leaky Rectified Linear Unit (ReLU) activation function:

$$y = \begin{cases} x & \text{if } x \geq 0 \\ 0.01x & \text{if } x < 0 \end{cases} \quad (1)$$

to ensure that such a small network does not "die out" since normal ReLUs, once deactivated, cannot be reactivated during gradient descent [21]. The invention is not particularly restricted to the use of this function only. Other suitable functions could be used as necessary. Advantageously, ReLUs are also fast to compute, and do not suffer from the vanishing/exploding gradient problem [21] as compared to the classic sigmoid function.

Figure 13:
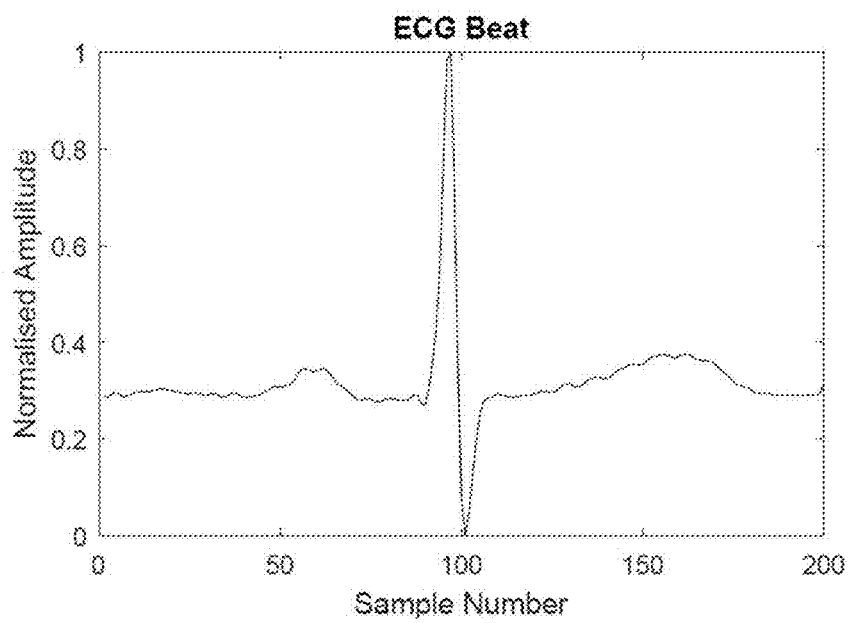
FIG. 13 illustrates a single extracted beat according to one embodiment of the present invention.

FIG. 13 illustrates a single extracted beat according to one embodiment of the present invention.

In one embodiment, the pinch point of width 20 was chosen after considering the number of parameters needed to describe the signal, and giving some room for other parameters not considered. The minimum number of parameters comprises 8 timings—start of P, end of P, Q, R, S, start of T, end of T—hence 7 time intervals, 5 amplitudes—P, Q, R, S, T—for a total of 12 parameters. With additional parameters, it allows for more subtle differences in waveforms to be encoded. and although 15 was tried, 20 was found to give a preferable result. A number over 20 could be also used as long as it fulfils the overall requirement of the methodology.

For training, 1 hour extracts from 10 files from the NSR database, 10 files from the AF database, and 3 files of personal recording (NSR) using the BITalino were downloaded and had single beats extracted. These recordings were all from lead I, II, or III only. 100% of all beats from the AF files that were not too noisy were used (pruned by variance thresholding of the signal), together with beats from the NSR files such that the data set had a ratio of approximately 60% normal 40% AF, giving a total of 96352 beats for the training set, with an additional 10000 beats reserved for the testing set. 50-50 ratio was not used so as to give a slightly larger set in hopes of better training while not having too strong a bias towards NSR beats.

The neural network was then trained using stochastic gradient descent and the quadratic cost function, with the option of weight decay (but was not found to be necessary). Note that with a small network as such, there are only 44200 parameters (weights) in the network, which is less than half of the number of training samples.

After training of the auto-encoder is complete, the neural network is then split and the output from the pinch point of 20 neurons is treated as a feature vector, which is a compact representation of the signal. This allows great flexibility in extensions of this technique to use any preferred classifier to operate on the feature vector.

Although the above mentioned neural network includes 20 nodes at the pinch point, other numbers of nodes are also possible. Other configurations for the neural network are also possible, for example, a neural network configuration of 301-100-30-100-301 could also be possible.

IV. C. Feature Extraction of Single ECG Beats

For AF detection, the need is to identify if the P wave is present or absent in each beat. Since the waveforms in the database are not marked at beat resolution, 500 AF beats and 600 non AF beats (considered as "normal") were laboriously identified by hand, shuffled into each other, and separated with 900 used for training with 200 reserved for testing.

A second neural network of 20-20-20-1 was then trained on the output of the feature extraction network using stochastic gradient descent and quadratic cost function, with weight decay which was necessary to prevent over-fitting. A support vector machine with a Gaussian kernel was also trained to allow comparison and assessment.

V. Results and Performance

V. A. Accuracy of QRS Detection

Generally speaking, the QRS beat annotations are taken from the database and compared with the ones generated using the matched filtering and QRS identification algorithm described in Section IV. A. In one embodiment, if the QRS annotations match within 50 ms, it is considered a hit, otherwise it is a miss. Using arbitrarily 2 records of AF and 2 of NSR (for example), the accuracy achieved by the algorithm was found to be 99.10% and 97.14% for the AF records, and 99.51% and 99.76% for the NSR records.

V. B. Performance of R-R Interval Diagnosis of AF

Figure 14:
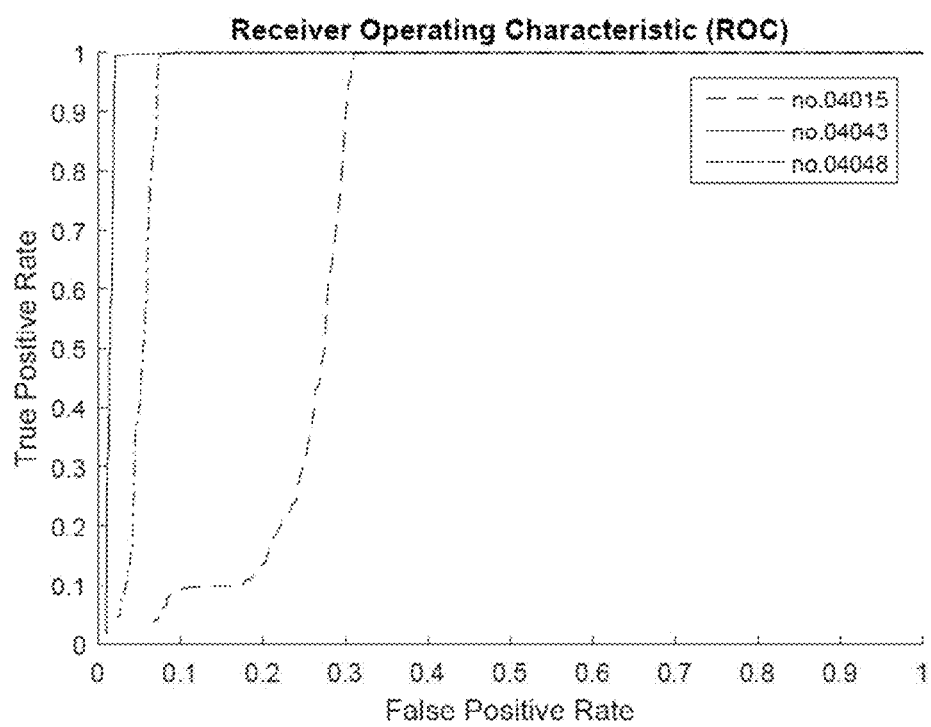
FIG. 14 illustrates a receiver operating characteristic curve for several AF records according to one embodiment.

FIG. 14 illustrates a receiver operating characteristic curve for several AF records according to one embodiment. Parameters for classifying R-R intervals as uneven were found by plotting Receiver Operating Characteristic (ROC) curves for several records and finding a threshold level that gave as close as possible to the optimum across all curves. This turned out to be 0.14 s, i.e. the sum of absolute differences between 4 R-R consecutive intervals (3 differences) as explained in Section IV. A.

The results vary greatly depending on the patient's inherent stability of heart rhythm. At the selected threshold value of 0.14 s, the detection rate is, for a representative selection of sample records, as summarised in Table 1.

TABLE 1

True and false positive rates for representative sample records using the R-R algorithm

| Record no. | True Positive | False Positive |
|---|---|---|
| (Unseen Sources) | | |
| 08378 | 97.84% | NA (all AF) |
| 08434 | 99.39% | 23.20% |
| 08455 | 99.32% | 5.78% |
| 17453 | NA (all NSR) | 17.57% |
| (Training Sources) | | |
| 04015 | 98.43% | 30.87% |
| 04048 | 99.64% | 7.57% |
| 04746 | 99.56% | NA (all AF) |
| 16265 | NA (all NSR) | 8.18% |

The high false positive rate is not too much of a concern since diagnosis of AF requires more than one factor, and hence the models will be combined. In doing so, all detection rates will go down, so it is desirable that the true positive rate is very high to begin with.

V. C. Performance of Reconstruction Using the Auto-Encoder

Figure 15:
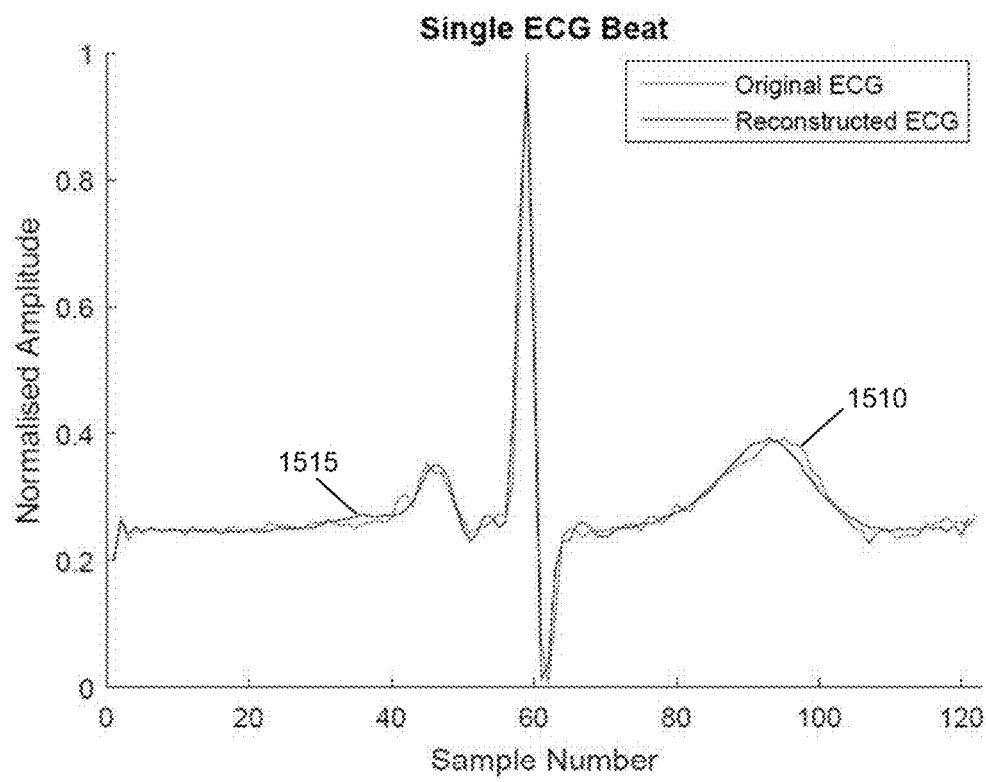
FIG. 15 illustrates an overlaid input ECG beat and auto-encoder reconstructed beat.

FIG. 15 illustrates an overlaid input ECG beat 1510 and auto-encoder reconstructed beat 1515. The fully trained auto-encoder appears to quite accurately reconstruct the given signal visually, and also seems to implement a de-noising filter to the incoming ECG beat (FIG. 15). The mean-squared error for beats is 0.055 in the training set, and 0.054 in the test set.

V. D. Feature Extraction Result

Figure 16:
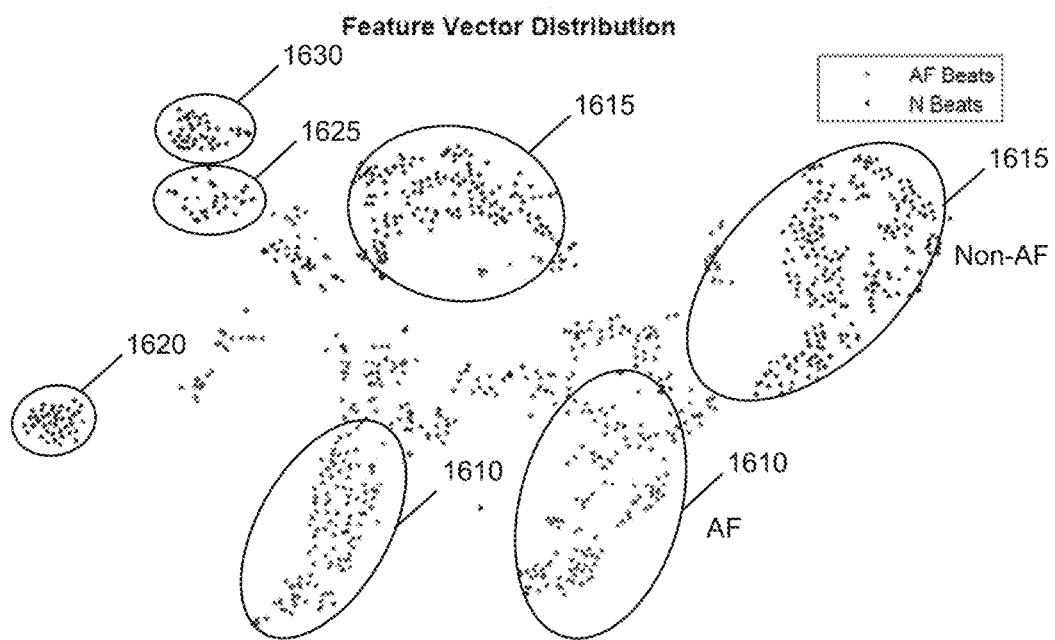
FIG. 16 illustrates a visualization of feature vector distribution using t-SNE according to one embodiment of the present invention.

FIG. 16 illustrates a visualization of feature vector distribution using t-SNE according to one embodiment of the present invention. The auto-encoder was split at the pinch point to create a feature extraction network which generates feature vectors of dimension 20. Of the hand-identified beats, 1000 of them were passed through the network, and then plotted using t-Distributed Stochastic Neighbour Embedding (t-SNE) [22] using the MATLAB script [23] written for it, with a perplexity of 40. The error at convergence of the t-SNE algorithm for the following plot (FIG. 16) is 0.42.

As can be seen, the feature extraction quite cleanly separates the AF beats from the normal (non AF) beats. There are a number of stray beats within the cluster, which could very well be mistakes in identification by hand. Nevertheless, the distribution of these clusters points to a good result in feature extraction.

Figure 17:
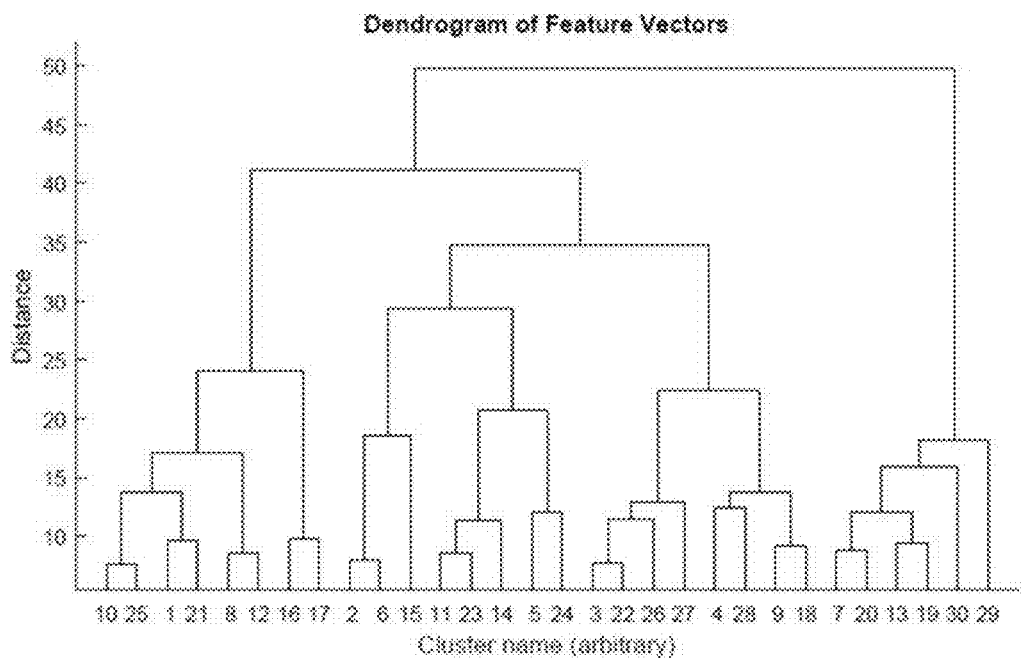
FIG. 17 illustrates Dendrogram of t-SNE projection down to 30 clusters according to one embodiment of the present invention.

FIG. 17 illustrates Dendrogram of t-SNE projection down to 30 clusters according to one embodiment of the present invention. The Dendrogram displays the hierarchical clustering of the distribution of feature vectors using the Euclidean distance between data points. There appears to be around 5 distinct clusters (distance between 25 and 30) when they are well separated, and at any lower distance than that splits up quickly into smaller clusters. However, if these 5 clusters are visualised (FIG. 16), while the bulk of most AF beats are captured, the smaller 3 or 4 clusters of AF seen in FIG. 16 are not distinguished from the normal beats. In order for the smaller clusters of AF to be assigned to separate clusters, for this projection using t-SNE, it was found desirable to go down to for example 12 clusters. However, the skilled person would appreciate that the invention is not restricted to the number of clusters mentioned above.

On several runs of t-SNE visualisation, the distribution pattern remained similar, fluctuating between 4 or 5 distinct main clusters. Similarly, the Dendrogram reflected that. This shows the consistency of t-SNE visualisation and shows that the feature extraction by the neural network does indeed separate the data set into well-formed clusters.

Figure 18:
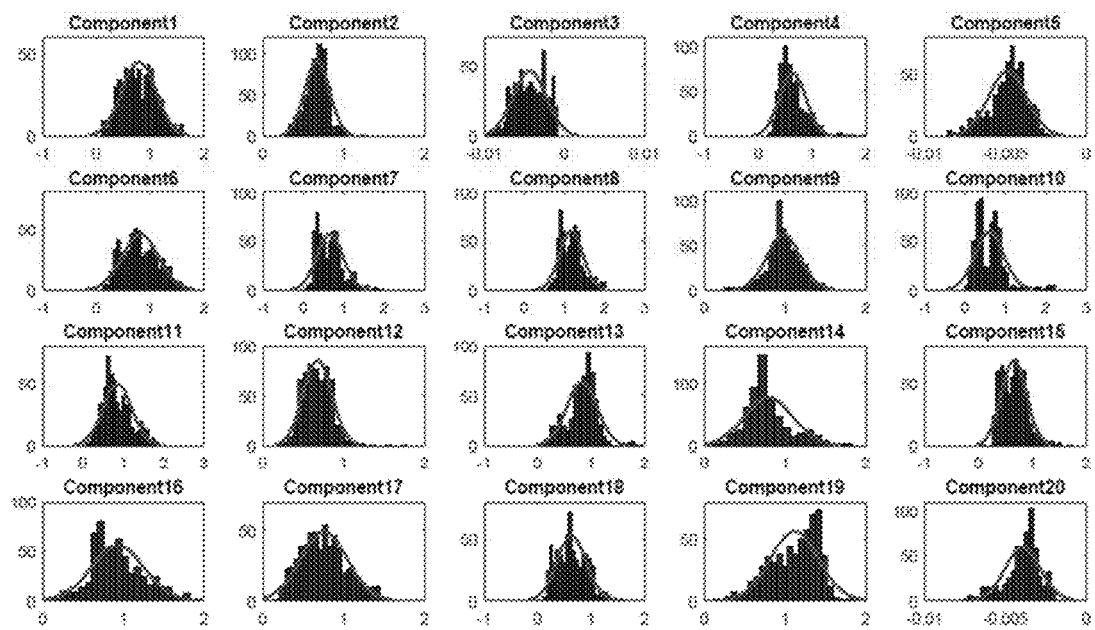
FIG. 18 illustrates a distribution of components of feature vector for NSR beats according to one embodiment.
Figure 19:
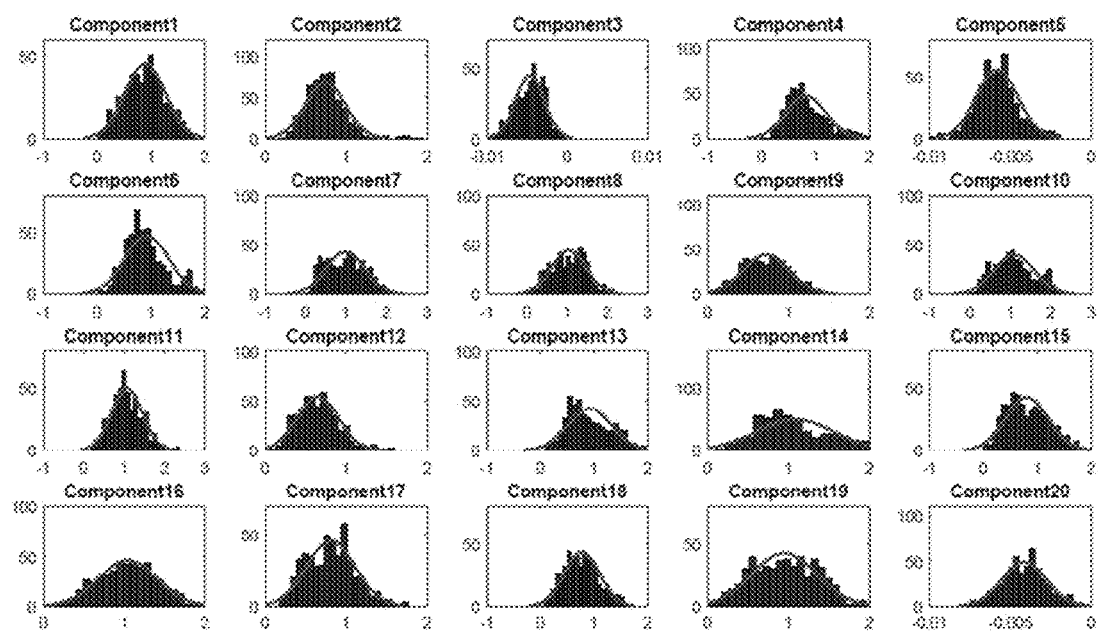
FIG. 19 illustrates a distribution of components of feature vector for AF beats according to one embodiment.

FIG. 18 illustrates a distribution of components of feature vector for NSR beats according to one embodiment. FIG. 19 illustrates a distribution of components of feature vector for AF beats according to one embodiment. The distribution of values for each feature in the feature vector was also inspected (FIGS. 18 and 19) in an attempt to spot any clear trends. In general, it can be observed that the values for each feature in AF beats have a wider distribution, and a lower mode. This could be due to the fact that AF is an irregularity in the heart. Since irregularities have many ways of occurring, the values could be more varied statistically, leading to a wider variance in the values of the feature vector. However, no specific component could be found to directly influence the waveform or be responsible for AF.

V. E. Performance of Neural Network Classifier

Figure 20:
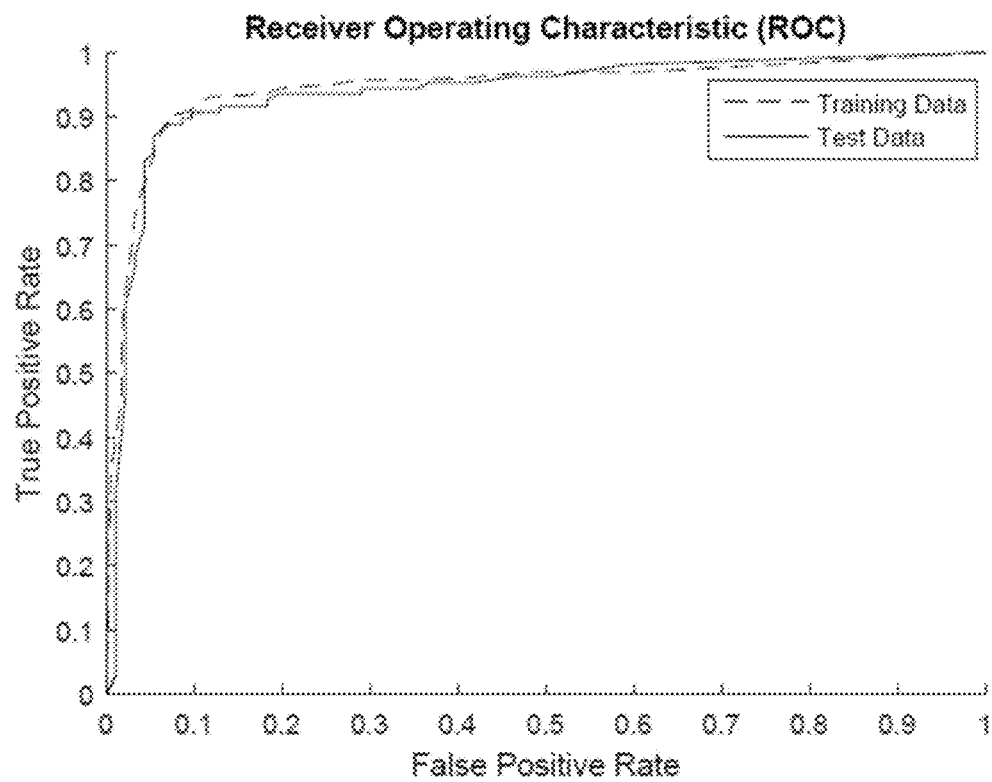
FIG. 20 illustrates a receiver operating characteristic curve of the neural network classifier for detecting absence of P waves.

FIG. 20 illustrates a receiver operating characteristic curve of the neural network classifier for detecting absence of P waves. The ROC curve (FIG. 20) was generated by varying the decision boundary on the neural network classifier output. The curve (test data) has an optimum point (furthest from the line of no-discrimination) at 88.8% true positive rate with a 6.5% false positive rate. This translates to a sensitivity of 88.8% and specificity of 93.5%.

Figure 24:
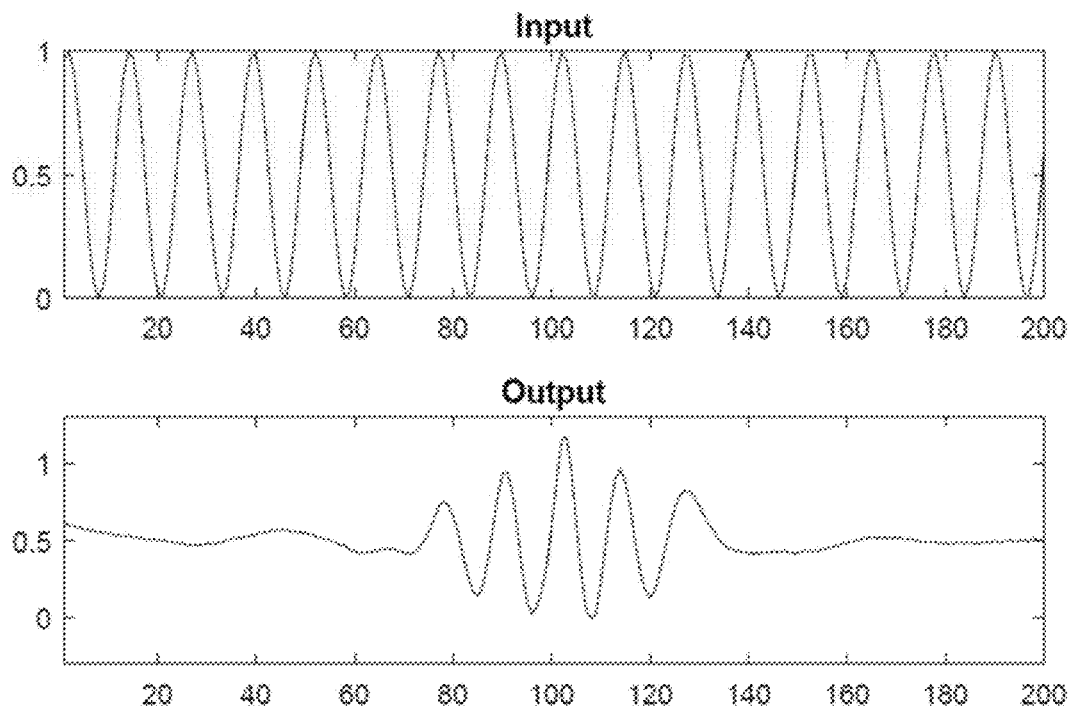
FIG. 24 illustrates a response of the auto-encoder to a sine wave input according to one embodiment.

The area underneath the curve is 0.938. The performance of the network was also checked on an unseen record (FIG. 24 shows an excerpt) that had no beats taken from it for the training set or the test set. This could very likely be due to mistakes in the hand-classified data that it is trained on. However, this would not alter the scope of the invention.

Figure 21:
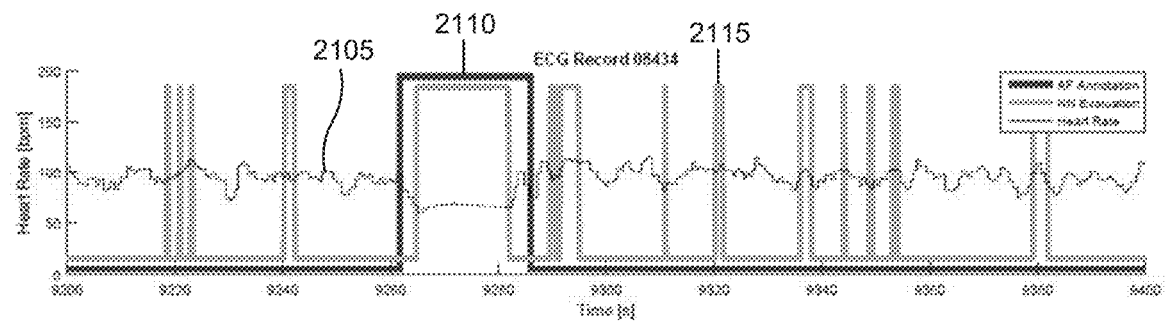
FIG. 21 illustrates a neural network classification on unseen ECG data records according to one embodiment.

FIG. 21 illustrates a neural network classification on unseen ECG data records according to one embodiment. The performance of the network was also checked on an unseen record (FIG. 21 shows an excerpt) that had no beats taken from it for the training set or the test set. Since each record is produced by a single patient, the ECG used in this test is from a different source. This is to test against overtraining.

In FIG. 21, the neural network evaluation (NN evaluation) 2115 returns a score which relates to how likely a P wave is present, from approximately 0 to 1 although values below 0 and above 1 are possible due to the nature of the leaky ReLU function (Equation (1)). The raw score output of the neural network is averaged over a window of 3 seconds, and then thresholded at 0.5 to give a high or low binary output. Thus, as seen in FIG. 21 under "NN Evaluation" 2115, "high" indicates that the P wave is present (not AF), and a "low" indicates that the P wave is absent (AF).

The record was annotated from the database to have a "normal" section in the middle from 9262 s to 9286 s with both sections on either side being AF. This is represented in FIG. 21 by the "AF Annotation" line being high when the rhythm is normal, and low when it is AF, in the same format as "NN Evaluation" 2115.

As can be seen from the figure, the classifier returns a solid "high" for the section labeled normal, except at the edges where the heart rate is also not quite constant. For the AF sections 2110, there appear to be a number of false negatives, but in general, the classifier is able to identify the abnormal beats. This can be seen from the overall graph of 1 hour (FIG. 22).

Figure 22:
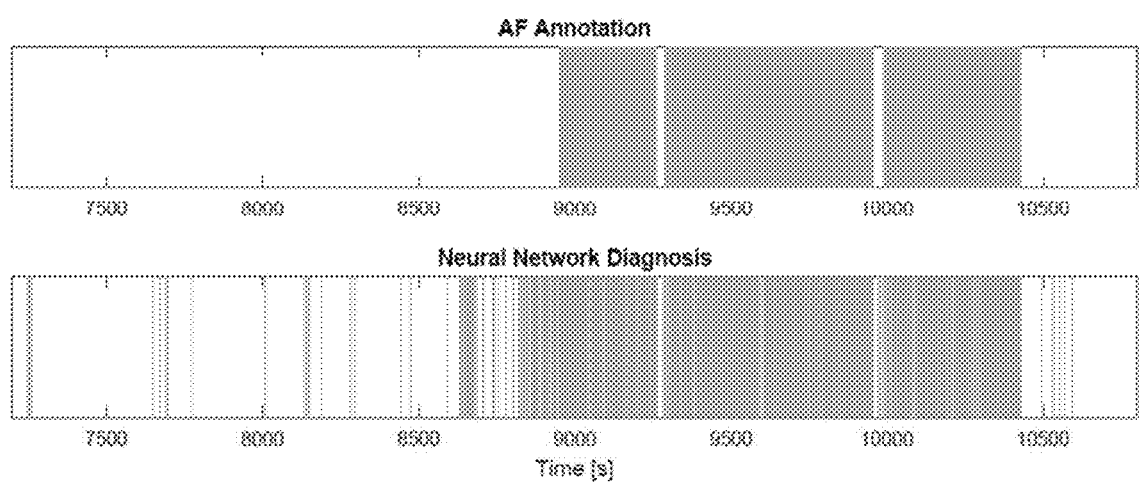
FIG. 22 illustrates a comparison between neural network and AF annotation for 1 hour.

FIG. 22 illustrates a comparison between neural network and AF annotation for 1 hour. Shaded regions indicate AF. Comparing the database annotated beats against the diagnosis by the neural network results in true and false positive rates, for a representative selectin of sample records, as shown in Table 2. The threshold of 0.5 was not adjusted to the optimum stated in the ROC curve because there is time averaging in place in this test, thus the ROC curve (for single beats) shown in the previous section is not applicable.

TABLE 2

True and false positive rates for representative sample records using the neural network

| Record no. | True Positive | False Positive |
|---|---|---|
| (Unseen Sources) | | |
| 08378 | 99.30% | NA (all AF) |
| 08434 | 94.52% | 14.37% |
| 08455 | 98.98% | 6.70% |
| 17453 | NA (all NSR) | 1.75% |
| (Training Sources) | | |
| 04015 | 100% | 23.55% |
| 04048 | 100% | 1.41% |
| 04746 | 98.53% | NA (all AF) |
| 16265 | NA (all NSR) | 0.11% |

As a cautionary note, because not every single beat is annotated in the database, but only in sections, the percentages reported are only showing how well the algorithm matches this broad marking category. Upon inspection of the ECG signal at areas of false negatives and positives, several beats were found that are likely correctly identified by the neural network, but were not marked by the database annotations. These beats are usually single or a small group of 2 to 4 (refer to Section VI. D. for examples).

Since the annotations were prepared by hand, it is highly plausible that the cardiologist would have missed these very small episodes, or did not consider them significant since they are too short. This may explain the high false positive rate. See Section VI. D. for full discussion.

V. F. Performance of Support Vector Machine

Figure 23:
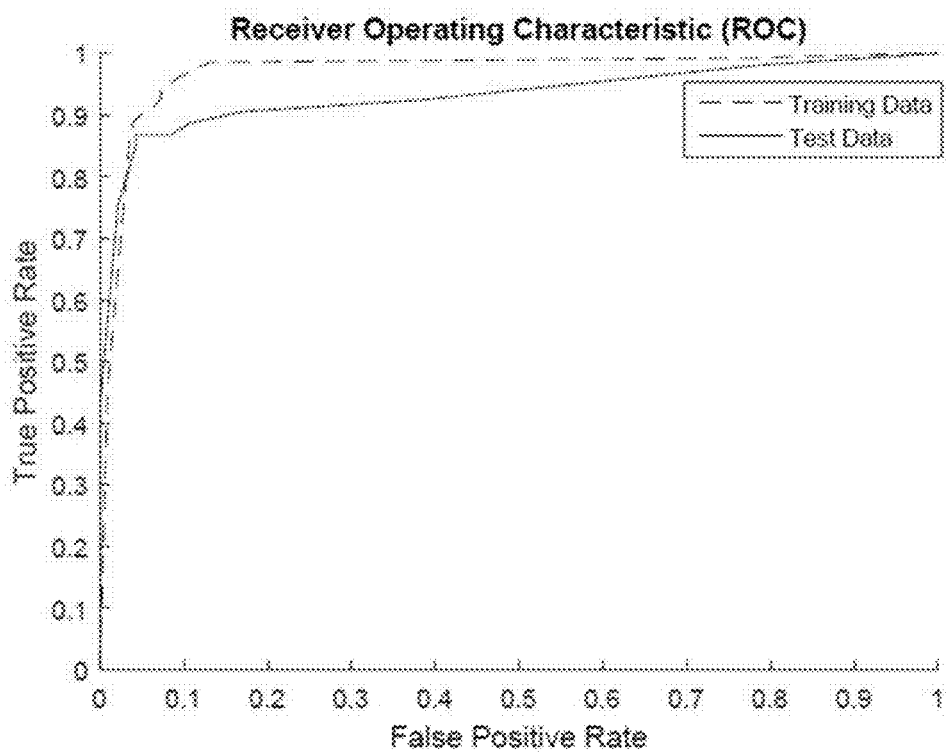
FIG. 23 illustrates a receiver operating characteristic curve of the support vector machine for detecting absence of P waves.

FIG. 23 illustrates a receiver operating characteristic curve of the support vector machine for detecting the absence of P waves. An ROC curve for the support vector machine with a Gaussian kernel was generated (FIG. 23) by varying the decision boundary. For example, the optimum point for this curve (test data) is at 86.8% true positive rate with a 4.3% false positive rate, translating to a sensitivity of 86.8% and a specificity of 95.7%. The area under the curve is 0.935. From the observation of the training data curve lying much higher than the test data curve, it can be inferred that the support vector machine over-fits the training set significantly more than the neural network, although both forms of classifiers perform almost equally, with the neural network being slightly better in sensitivity without trading off as much specificity above the optimum operating point.

V. G. Performance of Combined AF Metric

The combined AF metric consists of the irregular R-R interval flag and the neural network classifier flag. If both are flagged, the beat is identified as AF (which obeys the definition). Otherwise, it is identified as not AF (normal). This is equivalent to using a product of experts model, except with each expert output being binary.

With the combined AF metric, the results, for a representative selection of sample records, are as shown in Table 3.

TABLE 3

True and false positive rates for representative sample records using the combined AF metric

| Record no. | True Positive | False Positive |
|---|---|---|
| (Unseen Sources) | | |
| 08378 | 97.45% | NA (all AF) |
| 08434 | 94.52% | 14.37% |
| 08455 | 98.98% | 3.40% |
| 17453 | NA (all NSR) | 1.25% |
| (Training Sources) | | |
| 04015 | 98.43% | 23.40% |
| 04048 | 99.64% | 1.41% |
| 04746 | 98.09% | NA (all AF) |
| 16265 | NA (all NSR) | 0.11% |

Due to the R-R interval algorithm having high true positive rate and also a high false positive rate, the overall metric detection rate remains almost unchanged when compared to the neural network performance for true positive, but the false positive rates decrease slightly for some records (e.g. record 08455).

The sensitivity (true positive) and specificity (1—false positive) of the Holter monitor software (the competing product) are known to be approximately 95% and 75% respectively. Thus, the sensitivity of the combined AF metric is comparable, while the specificity is also comparable at worst, but offers a significant improvement at best.

VI. Further Discussions

VI. A. Auto-Encoder Analysis

Since the neural network is fully connected, it is difficult to understand what each of the individual parameters of the feature vector corresponds to. To understand the autoencoder better, several test signals were passed through to observe what reconstruction was at the output, such as sine waves, step inputs, and impulses of varying widths, much like analysing a control system.

FIG. 24 illustrates a response of the auto-encoder to a sine wave input according to one embodiment. The high frequency sine wave of unit amplitude on the input of the auto-encoder is only seen on the output at the middle, while the sides are attenuated to the mean of the signal (0.5). The frequency of the output in the middle remains unchanged, with zero phase shift. Thus, the auto-encoder can be interpreted as a linear filter with an "all pass filter" in the middle, and "low pass filters" at the sides.

Figure 25:
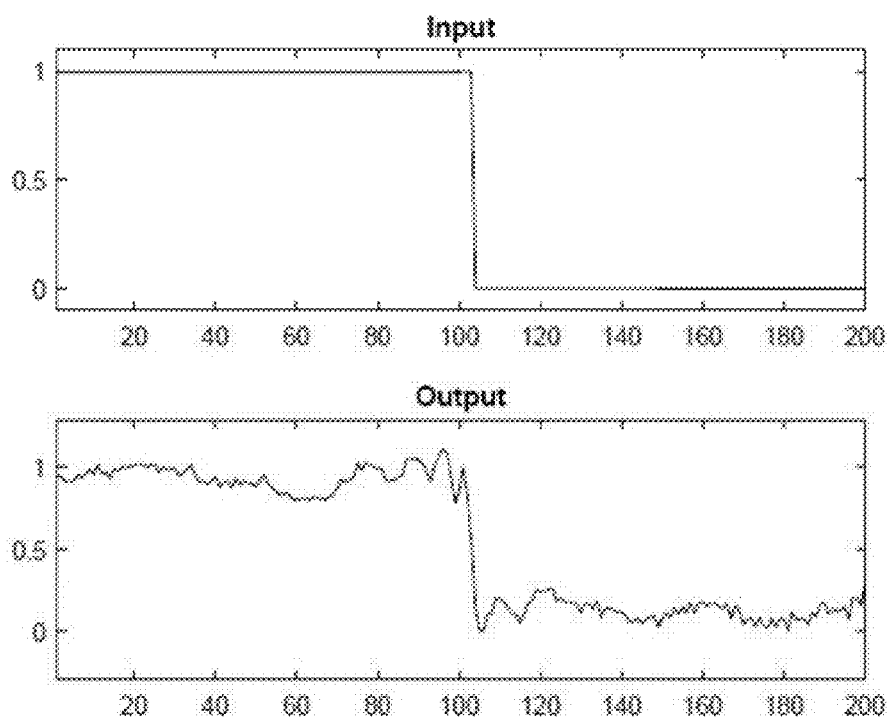
FIG. 25 illustrates a response of the auto-encoder to a step input in the middle according to one embodiment.
Figure 26:
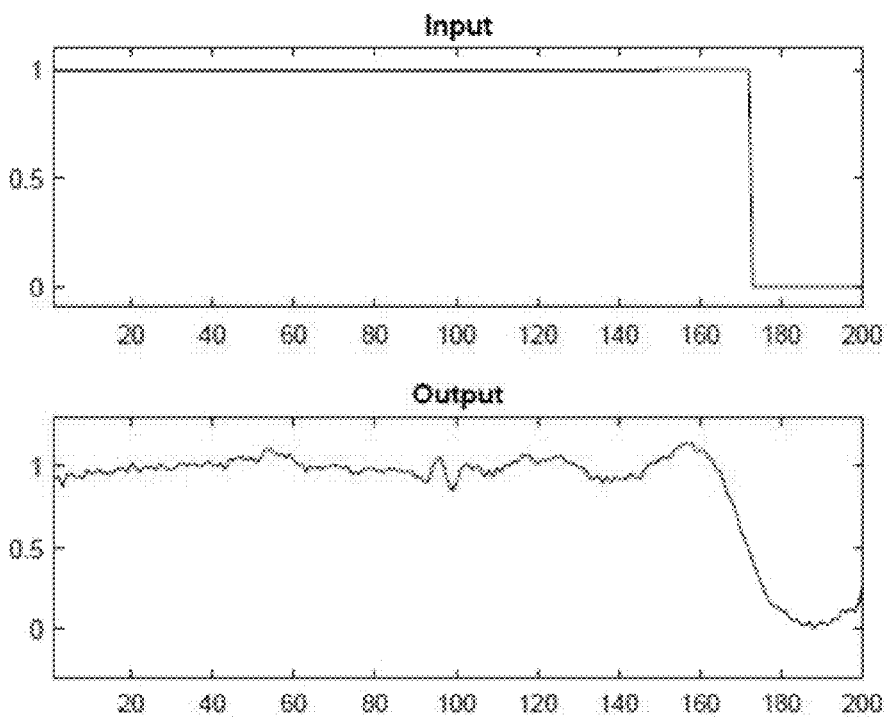
FIG. 26 illustrates a response of the auto-encoder to a step input at the side according to one embodiment.

FIG. 25 illustrates a response of the auto-encoder to a step input in the middle. FIG. 26 illustrates a response of the auto-encoder to a step input at the side. As can be seen, by comparing the output for a step function with the step in the middle (FIG. 25), which shows a sharper and steeper step along with some "ringing" artefacts, than at the side (FIG. 26), which is smoother, not as steep, also with ringing artefacts, but of lower frequency.

Intuitively, this makes sense since the ECG signal fed into the auto-encoder usually has the QRS complex in the middle, which has more high frequency components than the other parts of the ECG signal. In order to effectively encode such a signal, the auto-encoder has to therefore dedicate more of its capacity to the high frequency QRS complex in the middle, which explains why it acts as a "high pass filter", while dedicating less of its capacity to the lower frequency components, the P and T waves, by the sides.

VI. B. Feature Extraction Clustering

Besides the very apparent divide between AF and non-AF beats shown in FIG. 16 in Section V. D., it was found through inspection that the clusters themselves also group together beats of similar characteristics.

Figure 27:
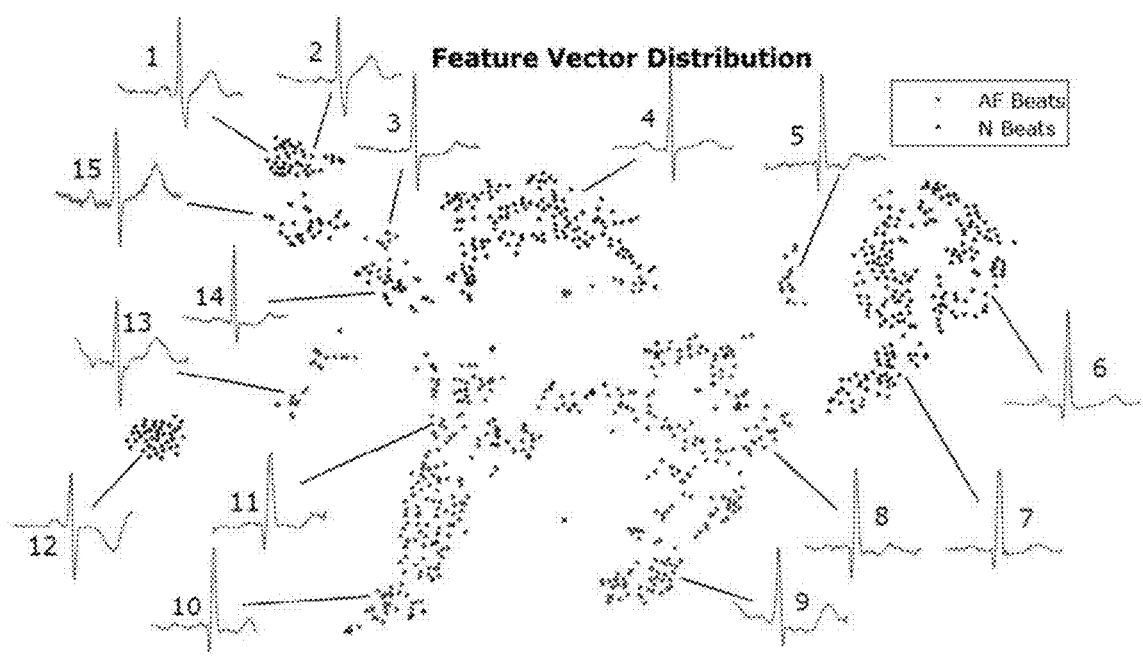
FIG. 27 shows a sample of a typical beat in each cluster according to one embodiment.

FIG. 27 shows a sample of a typical beat in each cluster. In this figure, the top left cluster with samples 1 and 2 is taken from the same cluster. Firstly, sample 2 has a P wave that is most likely present, and hence is likely a mistake in hand classification. This shows that the feature extraction network can help correct errors, and is possibly more reliable than visual inspection.

Secondly, the cluster that samples 1 and 2 belong to is a cluster of beats which suffer from Right Bundle Branch Block (RBBB). This is characterised by a widened dip of the S wave of the QRS complex, and is an abnormality, although it is marked as "normal" for the purposes of AF detection since it is not AF.

Lastly, both samples 1 and 2 appear to be mostly similar, showing that the cluster contains beats with similar characteristics, and hence the feature extraction does extract characteristics of the ECG beat well.

Other observations are that sample 12 belongs to the cluster with inverted T waves, which is abnormal, and generally the beats in the top left of the map have deep S waves, while the beats on the right side have deep Q waves (which is an abnormality). The only "perfect" normal ECG beat cluster is the one which sample 4 belongs to.

All of these observations point to the neural network feature extraction being very effective in characterising ECG beats. Thus, this forms a foundation from which classifiers can use the feature vector generated to easily distinguish between different types of abnormal beats, and not just AF.

VI. C. Computational Complexity

For purposes of real-time application, the computational complexity and load for running the algorithm analysis on the ECG signal has to be analysed. Because the algorithms developed are very simple inherently, the load is expected to be fairly low.

In one example, signals can be resampled to 200 Hz to ensure enough resolution, and capture most of the frequency content of the ECG, while not presenting too high a computational load. Note that the ECG equipment used in generating the PhsyioNet data has an upper band limit of 40 Hz (Nyquist of 80 Hz) [13], although the records are usually made with sample rates ranging from 125 Hz to 250 Hz. It will be appreciated that the invention is not limited to these frequencies.

The combined AF metric generally utilizes the use of both algorithms to function. At the base, both algorithms require QRS detection, which is a matched filter involving a convolution with a small kernel (for example, size 15 at 200 Hz sampling rate for example). This uses 15 multiplications per sample at 200 Hz (with computational complexity $0(n^2)$ with sampling rate, since the kernel size changes as well). Adaptive thresholding is then used to extract the QRS peaks, and requires 3 multiplications per sample regardless of sample rate, hence computational complexity $O(n)$.

The irregular R-R interval detection algorithm only does addition and subtraction to compute the absolute sum of all differences for every 4 intervals. This is dependent on heart rate, which is independent of sample rate, and hence of computational complexity $0(1)$.

In one example, the Neural Network, being of structure 201-100-20-20-20-1, requires a total of 22920 multiplications and additions per heartbeat, but is independent of sample rate, because each heartbeat is resampled to fit into 200 samples to be fed in to the neural network. Thus it has computational complexity $O(1)$.

The resampling itself uses interpolation, but is again independent of sampling frequency (computational complexity $O(1)$), since it depends on the number of out-puts which is fixed due to the requirement of the neural network, rather than inputs. If it is a linear interpolator, 200 samples of output requires 200 multiplications and 400 additions per heartbeat.

Lastly, combining both metrics involves a multiplication every heartbeat, again independent of sample rate (computational complexity $O(1)$).

As can be seen, apart from the QRS detection algorithm, both algorithms down the pipeline are dependent on heart rate rather than sample rate. Since common heart rates do not vary by much (e.g. factor of 3 from 60 at rest to 180 under intense physical activity), the total computational cost is of the order of tens of thousands of multiplications and additions per second. For today's processors of clock speeds in gigahertz, this is about 5 orders of magnitude less, which is indeed a very light load, and could potentially be performed entirely on the mobile phone instead of a centralized server.

VI. D. Accuracy of Database and Availability of Data

In one embodiment, the records in the MIT-BIH databases (both AF and normal) span around 10 hours each, presenting a great deal of data. However, there are relatively few number of records (i.e. sources): 25 for the AF database, and 18 for the NSR database. Of these, in the AF database, a number of the waveforms are not using lead I, II, or III. Because ECG waveforms vary greatly depending on where the electrode placements on the body are, algorithmic analysis has to be tailored for a particular waveform, hence some records are unusable. The last few records are also left out of training to be used as validation, since an independent source is best used for this purpose.

Anonymisation of the records in the databases also means that the phenotypes (age, gender, ethnicity, etc.) of the patients' records are unknown. This is significant because the similarities within a particular phenotype allow increased accuracy in detection algorithms in practice, due to common characteristics.

Only 1 hour is extracted from each record providing a few thousand beats to train on. Beats from the same patient do not vary considerably over the record, hence there is not much point training over the whole record. However, the 1 hour selected is not arbitrary, since each "AF record" is not entirely AF, but contains varying durations from just a few minutes in some records to several hours in others. The extracted hour is centered on the part of the record with the most amount of AF. Records with a very low duration of AF (or no long segments of AF) have instead, a section of NSR extracted, just to ensure variety of sources for training. This has been done due to observation that even in NSR sections, patients with AF have slightly unusual beat patterns.

Figure 28:
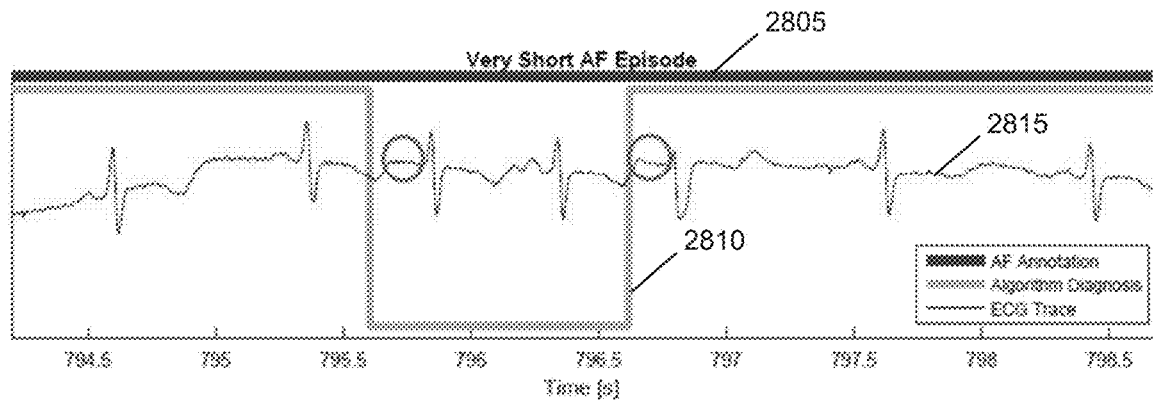
FIG. 28 illustrates a very short AF episode detected by the algorithm, but not annotated in the database according to one embodiment.

FIG. 28 illustrates a very short AF episode detected by the algorithm 2810, but not annotated in the database 2805. Circles indicate missing P waves. R-R intervals are also irregular in the ECG trace 2815. This result confirms that the technique of the present invention provides a significantly better result (or more sensitive result) compared to the conventional technique.

Figure 29:
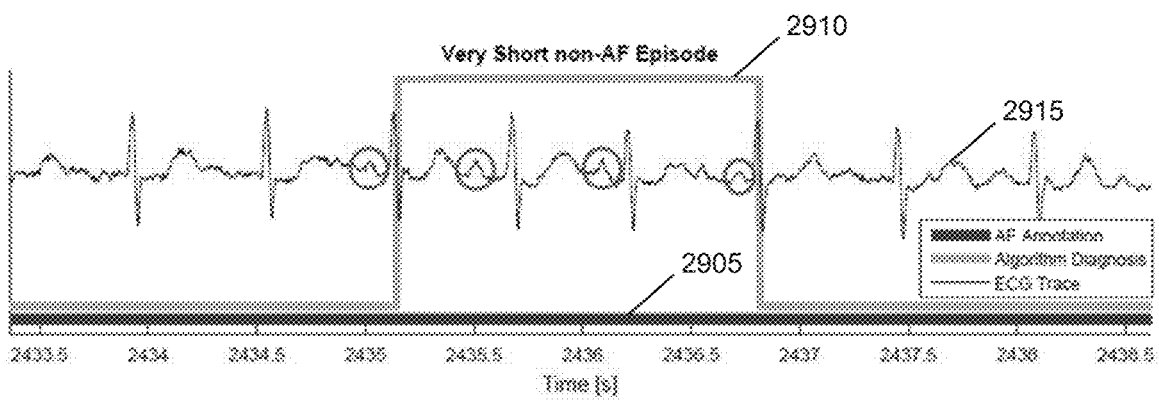
FIG. 29 illustrates a very short non-AF episode detected by the algorithm, but not annotated in the database according to one embodiment.

FIG. 29 illustrates a very short non-AF episode detected by the algorithm 2910, but not annotated in the database 2905. Circles indicate presence of P waves. R-R intervals are also quite regular in the ECG trace 2915.

It is clear that the annotations provided in the database are marked by hand, and only indicate broad sections (a minute or more), whereas the algorithm has been observed to pick up very short sections of the order of a few beats, which display abnormalities since it is operating on beat-level resolution (FIG. 28). The converse has also been observed, where in sections marked abnormal, there are very short sections of a few beats which appear to be not AF (FIG. 29). High output indicates non-AF while low output indicates detection of AF.

VI. E. Guarding Against Over-Fitting of Models

Generally speaking, the training and test set mentioned in Section IV. B. are separated by random selection from the total collection of beats, and are strictly non-interchangeable, i.e. the test set is never rotated in to the training.

Because the training and test set come from the same records, i.e. same sources, the final testing is done using a record that has not been used before. This prevents the algorithm parameters from learning the behaviour or signature of the source, which is a form of over-fitting. From the results garnered so far, it would appear that this is not an issue since similar detection rates are observed in both the seen and unseen sources. Nevertheless, this check is generally always be performed.

Training of the neural network is done, with each epoch, by randomising the order of the training set, and always only presenting a random subset to the network to learn on. This lowers the amount of time per epoch so that the network's performance may be assessed more frequently, and also helps with convergence. An epoch is considered as one complete cycle through all samples in the presented subset.

L2 regularisation (weight decay) is used only if over-fitting occurs without. In the auto-encoder, as mentioned in Section IV. B., the number of parameters in the neural network is less than half of the number of training samples. As such, no difference in training performance was observed with or without regularisation. However, for the classification network, over-fitting was observed to occur if no regularisation was used since the number of training samples was of the similar order of the number of parameters in the network.

VI. F. Limitations of Assessment Figures Presented

The figures of assessment provided are in relation to how close they match the AF annotations in the MIT-BIH databases. As mentioned earlier in Section VI. D., the database could be inaccurate in some areas since annotations are not beat level resolution, and no information is available about whether assessments of subclinical AF (that is, AF of durations shorter than as defined to be clinical AF) is also marked. From observations on AF annotations, subclinical AF is likely not annotated.

Thus, some of the false positives and false negatives could be attributed to real positives and negatives, but are penalised for not matching the AF annotations from the database, as demonstrated in Section VI. D., FIGS. 28 and 29. This highlights the potential for the algorithm to diagnose subclinical arrhythmias which has been shown to have significance [9], and help gather more data for assessment of the significance of subclinical arrhythmias.

As also mentioned, the number of sources in the database is few, although out of sample generalisation appears to perform well.

VI. G. Improving Classification Performance

There is currently no data available for classification of ECG traces at beat level and only 1000 beats that were verified by a single qualified medical doctor were used to train the classifier to distinguish between AF and non-AF. This is a very small sample size, and there are very likely a small number of errors in the classification by hand as well, as suggested by the cluster map. Having more hand-labeled beats by two or more qualified medical doctors will help improve the classification accuracy.

Currently, the autoencoder neural network is trained on the AF and NSR records from the PhysioNet database, which limits the various types of arrhythmias observed to mostly AF, with a few others such as RBBB (Right Bundle Branch Block).

It is possible that the classification network and the auto-encoder network could be trained together by sharing the first half of the network (feature extraction layers). This will not only encourage the feature extraction layer to learn features that represent the signal entirely, but also be incentivised to learn features that help discriminate among the various types of beats.

Classification of other types of arrhythmias could also be considered, building upon the feature extraction neural network which has a huge potential. Since the feature extraction cleanly clusters beats by characteristics, classifiers should find it easy to classify other types of arrhythmias as well. The feature extraction neural network also exhibits potential for unsupervised learning, which reduces the need for hand-labeled data.

The algorithm developed is able to function at beat-level resolution and thus paves the way for studies into extremely short durations of AF (e.g. single, double beat), at levels below even subclinical, which have been suggested to be possibly significant [9].

VII. Conclusions

Although the abovementioned description describes the use of various existing databases for training the first (auto-encoder) and second (classifier) neural networks, it will be appreciated that training is not dependent on these databases only. The machine learning technique utilised in the present invention is meant to use any source of data for training and diagnosis.

It will be appreciated that, for the auto-encoder structure, the present invention is not restricted to the dimension of 201-100-20-100-201. The general structure of an auto-encoder seeking to learn a compact representation is to start and end with the same dimensions, with a "pinch point" in the middle. Therefore, 301-100-30-100-301 or a similar dimension could be a possible configuration. That being said, the structure of 201-100-20-100-201 was arrived at, because, firstly, 200 (the extra 1 just being a scaling factor) will be equivalent to a sampling rate of 133 Hz at lowest if heart rates are around 40 bpm (very low by medical standards) when the scaling is applied. This is still well above the Nyquist frequency (80 Hz) to ensure no aliasing issues. Secondly, 20 is chosen as the pinch point because this number ideally should be as small as possible to achieve the most compact representation possible but yet ensure a good enough fit. Generally speaking, minimum number of parameters is above 12. Increasing this further gets better fit, but may lose generalisation abilities.

Regarding the classifier network, the structure of the network is not restricted to 20-20-20-1. Another possible structure could be 20-20-10-1 or 30-30-30-1. It is desirable to funnel down to 1.

In summary, the objective of developing an end-to-end system of hardware for collection of ECG signals, followed by transmission to a remote server (telemetry) and analysis for detection of AF, all in real time has been mostly demonstrated in the present invention.

The resolution of the algorithm down to beat level coupled with the high sensitivity that has been demonstrated in this invention allows the potential detection of subclinical AF which has significance in terms of risk of AF and risk of stroke. This paves the way for diagnosis of subclinical AF, and further studies into its significance.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

VIII. References

[1] "Arrhythmia", NHS, London, UK, 8 Jul. 2015. [Online]. Available: http://www. nhs.uk/conditions/arrhythmia/Pages/arrhythmia.aspx

[2] "The AF report. Atrial fibrillation—preventing a stroke crisis," Atrial Fibrillation Assoc., Warwickshire, Anticoagulation Europe, Kent, UK, 12 Apr. 2012. [Online]. Available: http://www.preventaf-strokecrisis.org/files/files/The_AF_Report_14_April 2012.pdf

[3] K. Carroll, S. Murad, J. Eliahoo, and A. Majeed, "Stroke incidence and risk factors in a population-based prospective cohort study," Office for National Statistics, Newport, South Wales, UK, Rep. Health Statistics Quarterly 12, 2001. [Online]. Available: http://www.ons.gov.uk/ons/rel/hsq/health-statisics-quarterly/no-12-winter-2001/stroke-incidence-and-risk-factors-in-a-population-based-prospective-cohort-study.pdf

[4] C. Marini et al., "Contribution of atrial fibrillation to incidence and outcome of ischemic stroke: results from a population-based study," *Stroke*, vol. 36, pp. 1115-1119, 2005. DOI: 10.1161/01.STR.0000166053.83476.4a

[5] D. M. Lloyd-Jones et al., "Lifetime risk for development of atrial fibrillation: the Framingham heart study," *Circulation*, vol. 110, no. 9, pp. 1042-1046, 31 Aug. 2004. DOI: 10.1161/01.CIR.0000140263.20897.42

[6] G. Y. H. Lip and H. S. Lim, "Atrial fibrillation and stroke prevention," *The Lancet Neurology*, vol. 6, no. 11, pp. 981-993, November 2007. DOI: 10.1016/S1474-4422(07) 70264-8

[7] M. Cesarelli, P. Bifulco, and M. Bracale, "An algorithm for the detection of the atrial fibrillation from the surface ECG for an of home-care evaluation of the implanted atrial defibrillators," in *Proc. Mediterranean Conf. Medical and Biological Eng. and Computing*, Cyprus, 1998. ARK: /87278/s6np23vh

[8] M. Carrara et al., "Classification of cardiac rhythm using heart rate dynamical measures: validation in MIT-BIH databases," *J. of Electrocardiology*, vol. 48, no. 6, pp. 943-946, November-December 2015. DOI: 10.1016/j.jelectrocard.2015.08.002

[9] J. S. Healy et al., "Subclinical atrial fibrillation and the risk of stroke," *The New England J. of Medicine*, vol. 366, no. 2, pp. 120-129, 12 Jan. 2012. DOI: 10.1056/NEJMoa1105575

[10] Williams Medical Supplies Ltd., Rhymney, UK. Welch Allyn HR-100 Holter and Software [Product]. [Online]. Available: http://www.wms.co.uk/ECGs/

[11] PLUX, Libson, Portugal. *BITalino* [Product]. (2013) [Online]. Available: http://www.bitalino.com

[12] D. G. Marquez, A. Otero, and M. Carlos, *Bitadroid* [Android application]. (2014) [Online]. Available: https://qithub.com/DavidGMarquez/Bitadroid

[13] PhysioNet, The MIT-BIH Atrial Fibrillation Database. [Online]. Available: https://physionet.org/physiobank/database/afdb/

[14] G. B. Moody and R. G. Mark, "A new method for detecting atrial fibrillation using R-R intervals," *Comput. in Cardiology*, vol. 10, pp. 227-230, 1983.

[15] PhysioNet, The MIT-BIH Sinus Rhythm Database. [Online]. Available: https://physionet.org/physiobank/database/nsrdb/

[16] M. Carrara, et al., "Heart rate dynamics distinguish among atrial fibrillation, normal sinus rhythm and sinus rhythm with frequent ectopy," *Physiological Measurement*, vol. 36, no. 9, pp. 1873-1888, September 2015. DOI: 10.1088/0967-3334/36/9/1873

[17] S. Ladavich and B. Ghoraani, "Developing an atrial activity-based algorithm for detection of atrial fibrillation," in *36th Annu. Int. Conf. IEEE Eng. in Medicine and Biology Soc.*, Chicago, Ill., USA, 2014, pp. 54-57. DOI: 10.1109/EMBC.2014.6943527

[18] I. Giller and E. D. Ubeyli, "ECG beat classifier designed by combined neural network model," *Pattern*

Recognition, vol. 38, no. 2, pp. 199-208, February 2005. DOI: 10.1016/j.patcog.2004.06.009

[19] T. Chou, Y. Tamura, and I. Wong, "Detection of atrial fibrillation in ECGs," Final Project, Dept. Comput. Sci., Stanford Univ., Stanford, Calif., USA, 2008. [Online]. Available:http://cs229.stanford.edu/proj2008/ChouTamuraWong-DetectionOfAtrialFibrillationInECGs.pdf

[20] S. Karpagachelvi, M. Arthanari, and M. Sivakumar, "ECG feature extraction techniques—a survey approach," Int. J. of Comput. Sci. and Inform. Security, vol. 8, no. 1, April 2010. arXiv: 1005.0957

[21] A. L. Maas, A. Y. Hannun, A. Y. Ng, "Rectifier nonlinearities improve neural network acoustic models," Proc. 30th Int. Conf. Mach. Learning, vol. 28 Atlanta, Ga., USA, 2013. [Online]. Available: http://ai.stanford.edu/~amaas/papers/relu_hybrid_icml2013_final.pdf

[22] L. J. P. van der Maaten and G. E. Hinton, "Visualising high-dimensional data using t-SNE," Journal of Mach. Learning Res., vol. 9, pp. 2579-2605, November 2008.

[23] L. J. P. van der Maaten, t-SNE Matlab implementation [MATLAB script]. [On-line]. Available: https://lvdmaaten.github.io/tsne/code/tSNE_matlab.zip

The invention claimed is:

1. A method of detecting abnormalities in electrocardiogram (ECG) signals, the method comprising: receiving a set of ECG signals from an ECG device; amplifying only the peaks of at least some of the set of ECG signals to produce ECG beat markings from which a heart rate is derivable to detect an irregular rhythm between at least two ECG beats; extracting a single ECG beat from the set of ECG signals from the ECG device by using said ECG beat markings; feeding the extracted single ECG beat into a first neural network; producing, at the first neural network, a compact representation of the extracted single ECG signal so as to generate a feature extraction output; and using, at a second neural network, the feature extraction output from the first neural network to generate a score associated with the abnormalities in the ECG signals.

2. A method according to claim 1, wherein said irregular rhythm is detected from an irregular R-R interval flag, and wherein the score generated at the second neural network determines the presence or absence of a P-wave in the ECG signals.

3. A method according to claim 2, wherein the method further comprises combining the irregular R-R interval flag with the score from the second neural network for identifying abnormalities in the ECG signals.

4. A method according to claim 1, wherein said amplifying only the peaks of at least some of the set of ECG signals is performed by a matched filtering technique.

5. A method according to claim 4, wherein the matched filtering technique reduces a base line wander of the set of ECG signals.

6. A method according to claim 4, wherein the matched filtering technique uses an algorithm comprising a first derivative of a Gaussian and/or a second derivative of a Gaussian.

7. A method according to claim 4, comprising applying an additive thresholding technique on the matched filtered signal which generates said ECG beat markings.

8. A method according to claim 1, wherein said extracting the single ECG beat is conducted by cutting between two consecutive R-R intervals.

9. A method according to claim 8, further comprising scaling the extracted single beat through resampling so that it fits into a predetermined number of samples.

10. A method according to claim 1, wherein at least one of the first and second neural networks is a feed forward artificial neural network.

11. A method according to claim 1, wherein the first neural network is trained as an auto-encoding neural network having a pinch point, and wherein said compact representation of the single ECG beat is obtained by splitting the auto-encoding neural network at the pinch point.

12. A method according to claim 11, wherein said compact representation of the single ECG beat is obtained by using a front end of the auto-encoding neural network.

13. A method according to claim 11, wherein an output from the pitch point of the auto-encoding network is a feature vector of a predetermined size, and optionally wherein the feature vector generates a plurality of clusters, wherein features associated with abnormalities are grouped in at least some clusters.

14. A method according to claim 1, wherein the second neural network is a trained classifier network which generates the score associated with the abnormalities relating to the presence or absence of P-wave in ECG signals.

15. A method according to claim 14, further comprising training a support vector machine with a Gaussian algorithm to compare the results from the classifier network.

16. A method according to claim 1, wherein the second neural network is a classifier network which determines any one of: (5) atrial fibrillation (AF); (6) inverted T-waves; (7) deep Q-waves; and/or (8) deep S-waves.

17. A method according to claim 1, further comprising a plurality of second neural networks, each determining a separate symptom from the following list: (5) atrial fibrillation (AF); (6) inverted T-waves; (7) deep Q-waves; and/or (8) deep S-waves.

18. A system for detecting abnormalities in electrocardiogram (ECG) signals, the system comprising: an ECG device configured to obtain a set of ECG signals; a mobile device configured to receive ECG signals from the ECG device; a server configured to receive ECG data from the mobile device; and a processing unit configured to process the set of ECG signals from the ECG device and detect abnormalities in the ECG signals;

wherein the processing unit comprises: an irregular rhythm detector for amplifying only the peaks of at least some of the set of ECG signals to produce ECG beat markings from which a heart rate is derivable to detect an irregular rhythm between at least two ECG beats; a beat extractor for extracting a single ECG beat from the set of ECG signals from the ECG device by using said ECG beat markings; a first neural network for receiving the extracted single ECG beat and for producing a compact representation of the extracted single ECG signal so as to generate a feature extraction output; and a second neural network for using the feature extraction output from the first neural network to generate a score associated with the abnormalities in the ECG signals.

19. A system according to claim 18, wherein the processing unit is located within the ECG device or the server.

* * * * *